United States Patent
Fichtali et al.

(10) Patent No.: US 8,048,652 B2
(45) Date of Patent: Nov. 1, 2011

(54) BIOMASS HYDROLYSATE AND USES AND PRODUCTION THEREOF

(75) Inventors: Jaouad Fichtali, Lexington, KY (US); Micah Hazzy Needham, Winchester, KY (US); Henry Linsert, Jr., Alexandria, VA (US)

(73) Assignee: Martek Biosciences Corporation, Columbia, MD (US)

( * ) Notice: Subject to any disclaimer, the term of this patent is extended or adjusted under 35 U.S.C. 154(b) by 0 days.

(21) Appl. No.: 11/433,752

(22) Filed: May 12, 2006

(65) Prior Publication Data

US 2006/0286205 A1 Dec. 21, 2006

Related U.S. Application Data

(60) Provisional application No. 60/680,740, filed on May 12, 2005, provisional application No. 60/781,430, filed on Mar. 10, 2006.

(51) Int. Cl.
*C12P 7/64* (2006.01)
(52) U.S. Cl. ............ 435/134; 435/257.1; 424/439
(58) Field of Classification Search ................. None
See application file for complete search history.

(56) References Cited

U.S. PATENT DOCUMENTS

| | | | |
|---|---|---|---|
| 4,731,248 A | 3/1988 | Hogan et al. | |
| 5,360,730 A | 11/1994 | Orndorff et al. | |
| 5,422,247 A | 6/1995 | Finkelstein et al. | |
| 5,547,699 A | 8/1996 | Iizuka et al. | |
| 5,656,319 A | 8/1997 | Barclay | |
| 5,885,819 A | 3/1999 | Kofod et al. | |
| 6,338,866 B1 * | 1/2002 | Criggall et al. | 426/549 |
| 6,693,188 B2 | 2/2004 | Bohlmann et al. | |
| 6,977,167 B2 | 12/2005 | Barclay | |
| 2002/0001833 A1 * | 1/2002 | Ruecker et al. | 435/134 |
| 2003/0143659 A1 * | 7/2003 | Bijl et al. | 435/67 |
| 2005/0170479 A1 * | 8/2005 | Weaver et al. | 435/134 |

FOREIGN PATENT DOCUMENTS

| | | |
|---|---|---|
| EP | 0427312 | 5/1991 |
| EP | 0463706 B1 | 3/2003 |
| WO | 00/15045 | 3/2000 |
| WO | 01/25411 | 4/2001 |
| WO | 02/24926 | 3/2002 |
| WO | 02/33055 | 4/2002 |
| WO | 03/007728 | 1/2003 |
| WO | 03/068002 | 8/2003 |
| WO | 03/068003 | 8/2003 |
| WO | 03/092628 | 11/2003 |
| WO | WO 03/105606 | 12/2003 |
| WO | 2004/040997 | 5/2004 |
| WO | 2005/013708 | 2/2005 |

OTHER PUBLICATIONS

Kailasapathy K., Curr Issues Intest. Microbiol, 2002, vol. 3 p. 39-48.*
Pulz et al., Appl Microbiol Biotechnol, 2004, vol. 65, p. 635-648.*
Gouin S., Trends in Food Science & Technology, 2004, vol. 15, p. 330-347.*
Harel et al., Aquaculture, 2002, vol. 213, p. 347-362.*
Mendes-Pinto et al., Journal of Applied Phycology, 2001, vol. 13, p. 19-24.*
Heinzelmann et al., Colloids and Surfaces B: Biointerfaces, 1999, vol. 12, p. 223-229.*
International Search Report and Written Opinion for PCT Application No. PCT/US06/18445, mailed Jul. 3, 2008.

* cited by examiner

*Primary Examiner* — Kade Ariani
(74) *Attorney, Agent, or Firm* — Sterne, Kessler, Goldstein & Fox P.L.L.C.

(57) ABSTRACT

The present invention includes a palatable, stable composition comprising a biomass hydrolysate emulsion for incorporation, into, or used as, nutritional products, cosmetic products or pharmaceutical products. Preferred sources for biomass are microbial sources, plant sources and animal sources. The present invention also provides methods for making such compositions, specifically, a method for producing a product comprising a nutrient, particularly a long chain polyunsaturated fatty acid, comprising hydrolyzing a biomass comprising the nutrient and emulsifying the hydrolyzed biomass. Such compositions and methods are useful, for example, for increasing intake of nutrients such as omega-3 long chain polyunsaturated fatty acids having 18 or more carbons.

24 Claims, No Drawings

BIOMASS HYDROLYSATE AND USES AND PRODUCTION THEREOF

CROSS-REFERENCE TO RELATED APPLICATIONS

This application claims priority under 35 U.S.C. §119(e) to U.S. Provisional Patent Application Ser. No. 60/680,740 filed May 12, 2005, which is incorporated herein in its entirety by this reference. This application also claims priority under 35 U.S.C. §119(e) to U.S. Provisional Patent Application Ser. No. 60/781,430 filed Mar. 10, 2006, which is incorporated herein in its entirety by this reference.

FIELD OF THE INVENTION

The invention relates to stable compositions comprising a biomass hydrolysate, in particular a hydrolysate comprising at least one long chain polyunsaturated fatty acid. The invention also relates to methods for making such compositions and nutritional, cosmetic and pharmaceutical products comprising said compositions, including compositions useful as delivery systems for bioactive or therapeutic compounds.

BACKGROUND OF THE INVENTION

It is desirable to increase the dietary intake of beneficial nutrients omega-3 polyunsaturated fatty acids (omega-3 PUFA), and omega-3 long chain polyunsaturated fatty acids (LC PUFA). Other beneficial nutrients are omega-6 long chain polyunsaturated fatty acids. As used herein, reference to a long chain polyunsaturated fatty acid or LC PUFA, refers to a polyunsaturated fatty acid having 18 or more carbons. Omega-3 PUFAs are recognized as important dietary compounds for preventing arteriosclerosis and coronary heart disease, for alleviating inflammatory conditions, cognitive impairment and dementia related diseases and for retarding the growth of tumor cells. One important class of omega-3 PUFAs is omega-3 LC PUFAs. Omega-6 PUFAs serve not only as structural lipids in the human body, but also as precursors for a number of factors in inflammation such as prostaglandins, and leukotrienes.

Fatty acids are carboxylic acids and are classified based on the length and saturation characteristics of the carbon chain. Fatty acids having 2 to 14 carbons are typically saturated. Longer chain fatty acids having from 16 to 24 or more carbons may be saturated or unsaturated. In longer chain fatty acids there may be one or more points of unsaturation, giving rise to the terms "monounsaturated" and "polyunsaturated," respectively. Long chain PUFAs are of particular interest in the present invention.

LC PUFAs are categorized according to the number and position of double bonds in the fatty acids according to a well understood nomenclature. There are two series or families of LC PUFAs, depending on the position of the double bond closest to the methyl end of the fatty acid: the n-3 series contains a double bond at the third carbon, while the n-6 series has no double bond until the sixth carbon. Thus, docosahexaenoic acid ("DHA") has a chain length of 22 carbons with 6 double bonds beginning with the third carbon from the methyl end and is designated "22:6 n-3". Other important omega-3 LC PUFAs include eicosapentaenoic acid ("EPA") which is designated (20:5 n-3) and omega-3 docosapentaenoic acid ("DPA" or "DPAn-3") which is designated (22:5 n-3). Important omega-6 LC PUFAs include arachidonic acid ("ARA") which is designated (20:4 n-6), and omega-6 docosapentaenoic acid ("DPA" or "DPAn-6") which is designated (22:5 n-6).

De novo or "new" synthesis of the omega-3 and omega-6 long chain essential fatty acids such as DHA and ARA does not occur in the human body; however, the body can convert shorter chain fatty acids to LC PUFAs such as DHA and ARA although at very low efficiency. Both omega-3 and omega-6 fatty acids must be part of the nutritional intake since the human body cannot insert double bonds closer to the omega end than the seventh carbon atom counting from that end of the molecule. Thus, all metabolic conversions occur without altering the omega end of the molecule that contains the omega-3 and omega-6 double bonds. Consequently, omega-3 and omega-6 acids are two separate families of essential fatty acids since they are not interconvertible in the human body.

Over the past twenty years, health experts have recommended diets lower in saturated fats and higher in polyunsaturated fats. While this advice has been followed by a number of consumers, the incidence of heart disease, cancer, diabetes and many other debilitating diseases has continued to increase steadily. Scientists agree that the type and source of polyunsaturated fats is as critical as the total quantity of fats. The most common polyunsaturated fats are derived from vegetable matter and are lacking in many long chain fatty acids (most particularly omega-3 LC PUFAs). In addition, the hydrogenation of polyunsaturated fats to create synthetic fats has contributed to the rise of certain health disorders and exacerbated the deficiency in some essential fatty acids. Indeed, many medical conditions have been identified as benefiting from omega-3 supplementation. These include acne, allergies, Alzheimer's, arthritis, atherosclerosis, breast cysts, cancer, cystic fibrosis, diabetes, eczema, hypertension, hyperactivity, intestinal disorders, kidney dysfunction, leukemia, and multiple sclerosis. Of note, the World Health Organization has recommended that infant formulas be enriched with omega-3 fatty acids.

The polyunsaturates derived from meat contain significant amounts of omega-6 but little or no omega-3. While omega-6 and omega-3 fatty acids are both necessary for good health, they are preferably consumed in a balance of about 4:1. Concerned consumers have begun to look for health food supplements to restore the equilibrium. Principal sources of omega-3s are flaxseed oil and fish oils. The past decade has seen rapid growth in the production of flaxseed and fish oils. Both types of oil are considered good dietary sources of omega-3 polyunsaturated fats. Flaxseed oil contains no EPA, DHA, or DPA but rather contains linolenic acid—a building block that can be elongated by the body to build longer chain PUFAs. There is evidence, however, that the rate of metabolic conversion can be slow and unsteady, particularly among those with impaired health. Fish oils vary considerably in the type and level of fatty acid composition depending on the particular species and their diets. For example, fish raised by aquaculture tend to have a lower level of omega-3 fatty acids than fish from the wild. In light of the health benefits of such omega-3 and omega-6 LC PUFAs, it would be desirable to supplement foods with such fatty acids.

Due to the scarcity of sources of omega-3 LC PUFAs, typical home-prepared and convenience foods are low in both omega-3 PUFAs and omega-3 LC PUFAs, such as docosahexaenoic acid, docosapentaenoic acid, and eicosapentaenoic acid. In light of the health benefits of such omega-3 PUFAs, it would be desirable to supplement foods with such fatty acids.

While foods and dietary supplements prepared with such PUFAs may be healthier, they also have an increased vulnerability to rancidity. Rancidity in lipids, such as unsaturated fatty acids, is associated with oxidation off-flavor development. The off-flavor development involves food deterioration affecting flavor, aroma, color, texture, and the nutritional value of the particular food. A primary source of off-flavor development in lipids, and consequently the products that contain them, is the chemical reaction of lipids with oxygen. The rate at which this oxidation reaction proceeds has generally been understood to be affected by factors such as temperature, degree of unsaturation of the lipids, oxygen level, ultraviolet light exposure, presence of trace amounts of pro-oxidant metals (such as iron, copper, or nickel), lipoxidase enzymes, free radicals and so forth.

The susceptibility and rate of oxidation of the unsaturated fatty acids can rise dramatically as a function of increasing degree of unsaturation. In this regard, EPA and DHA contain five and six double bonds, respectively. This high level of unsaturation renders the omega-3 fatty acids readily oxidizable. The natural instability of such oils may give rise to unpleasant odor and unsavory flavor characteristics even after a relatively short period of time.

As stated previously it is also desirable to increase intake of other beneficial nutrients. Various sources, including certain types of microalgae and fungi, as well as plant sources, e.g., seeds and animal sources, e.g., aquatic animals, are nutrient dense sources of glycoproteins, vitamins, minerals, simple and complex carbohydrates, antioxidants, amino acids, lipids and other bioactive compounds. However, the unpleasant taste and/or texture of some of these sources has precluded their widespread incorporation into food products. Furthermore, because of the complex biochemical nature of their cell walls, the digestibility of certain microorganisms and seeds and the resulting bioavailability of their nutrients would likely be limited if they were ingested whole and intact.

Instead, selected nutrients are typically extracted from these sources for use in nutritional and/or pharmaceutical products. For example, DHA-rich microbial oil is manufactured from the dinoflagellate *Crypthecodinium cohnii* and ARA-rich oil is manufactured from the filamentous fungus *Mortierella alpina*, both for use as nutritional supplements and in food products such as infant formula. Similarly, DHA-rich microbial oil from *Schizochytrium* is manufactured for use as a nutritional supplement or food ingredient. Typically, the LC PUFAs are extracted from biomass and purified. The extracted and purified oils can be further processed to achieve specific formulations for use in food products (such as a dry powder or liquid emulsion).

It would be desirable to produce a composition comprising nutrient-rich biomass in a form that is easily digested, that exhibits a high nutrient bioavailability, is stable in terms of oxidation, and has acceptable organoleptic characteristics. Especially desirable would be such a composition comprising a PUFA-rich microorganism that exhibits a high oxidative stability. It would be additionally desirable to produce such a composition that is available in either a liquid form or a dry form to accommodate a variety of food and pharmaceutical applications. It would be further desirable to provide a low cost method for making such a composition, said method involving the use of non-hazardous materials, minimal processing steps, and minimal raw material inventory.

SUMMARY OF THE INVENTION

The present invention provides a method for producing a product comprising a nutrient. The method includes hydrolyzing a biomass comprising the nutrient to produce a hydrolyzed biomass; and emulsifying the hydrolyzed biomass to form a stable product. The product may be a food product, a nutritional product, a multivitamin, or a pharmaceutical product.

In some embodiments, the product is dried. In some embodiments, the biomass or the hydrolyzed biomass is dried by membrane filter press drying, spray drying, fluidized bed drying, lyophilization, freeze drying, tray drying, vacuum tray drying, drum drying, vacuum mixer/reactor drying, excipient drying, solvent drying, fluidized spray drying, conveyer drying, ultrafiltration, evaporation, osmotic dehydration, freezing, absorbent addition, extrusion or a combination thereof. In some embodiments, the product is extruded.

In some embodiments, the method additionally includes the step of adding a stabilizing agent. The stabilizing agent may be microencapsulants, surfactants, emulsion stabilizers or a combination thereof. The microencapsulants may be cell particulates, gum acacia, maltodextrins, hydrophobically modified starch, polysaccharides, hydrophobically-modified polysaccharides, proteins, or combinations thereof. The surfactants may be anionic agents, cationic agents, nonionic agents, amphoteric agents, water insoluble emulsifying agents, finely divided particles and naturally occurring materials, or a combination thereof. The emulsion stabilizers may be emulsifiers, thickeners, or a combination thereof.

In some embodiments, the step of hydrolyzing the biomass may be enzymatic hydrolysis, chemical disruption, physical-mechanical disruption, physical-non-mechanical disruption or a combination thereof.

In embodiments utilizing enzymatic hydrolysis, the enzyme for hydrolysis may be xylanases, cellulases, amylases, carbohydrases, proteases, chitinases, lipases, or a combination thereof; including a protease, a carbohydrase, a chitinase or a combination thereof.

In some embodiments, the step of hydrolyzing the biomass is chemical disruption. The step of chemical disruption may be pH disruption, detergent disruption, solvent disruption, or a combination thereof.

In some embodiments, the step of hydrolyzing the biomass is physical-mechanical cell disruption. The physical-mechanical disruption may be ultrasonication, wet milling, high pressure homogenization, impingement, pressure extrusion, or a combination thereof. In some embodiments, the physical-mechanical disruption may be homogenization, wet milling, or impingement.

In some embodiments, the step of hydrolyzing the biomass is physical-non-mechanical cell disruption. The physical-non-mechanical cell disruption may be osmotic shock, freeze-thawing, drying, steam treatment, or a combination thereof.

In some embodiments, the method further comprises introducing browning reaction products to the hydrolyzed biomass. The introducing may be mixing browning reaction products into the hydrolyzed biomass or forming browning reaction products in the hydrolyzed biomass. Forming browning reaction products may be by heating the hydrolyzed biomass in the presence of browning reaction product precursors to form browning reaction products.

In some embodiments, the step of emulsifying may be by mechanical agitation, ultrasonic vibration, heating, or combinations thereof.

In some embodiments, the biomass comprises a microorganism which may be algae, protists, bacteria or fungi. In some embodiments, the microorganism is an oleaginous microorganism. In other embodiments, the microorganism may be microorganisms of the genus *Thraustochytrium*, microorganisms of the genus *Schizochytrium*, microorganisms of the genus *Althornia*, microorganisms of the genus

*Aplanochytrium*, microorganisms of the genus *Japonochytrium*, microorganisms of the genus *Elina*, microorganisms of the genus *Crypthecodinium*, microorganisms of the genus *Mortierella* or mixtures thereof. In some embodiments, the microorganism may be microorganisms of the genus *Schizochytrium*, microorganisms of the genus *Crypthecodinium*, microorganisms of the genus *Mortierella* or mixtures thereof.

In some embodiments, the biomass is derived from a plant source. In some embodiments, the plant source has been genetically modified to produce long chain polyunsaturated fatty acids, and the plant may be soybean, corn, safflower, sunflower, canola, flax, peanut, mustard, rapeseed, chickpea, cotton, lentil, white clover, olive, palm, borage, evening primrose, linseed or tobacco. In other embodiments, the plant source has not been genetically modified to produce long chain polyunsaturated fatty acids, and the plant may be soybean, corn, safflower, sunflower, canola, flax, peanut, mustard, rapeseed, chickpea, cotton, lentil, white clover, olive, palm, borage, evening primrose, linseed or tobacco.

In some embodiments, the biomass is derived from an animal source. The animal source may be aquatic animals, animal tissues or animal products.

In some embodiments of the method, the nutrient comprises an LC PUFA. In some embodiments, the nutrient comprises an LC PUFA having a carbon chain length of at least 18. In some embodiments, the LC PUFA has a carbon chain length of at least 22. In some embodiments, the LC PUFA has at least three double bonds. In other embodiments, the LC PUFA has at least four double bonds. In some embodiments, the LC PUFA may be docosahexaenoic acid, docosapentaenoic acid, arachidonic acid, eicosapentaenoic acid, or gamma-linolenic acid.

In some embodiments of the method, the product is a liquid emulsion. In some embodiments, the emulsion is more stable than the hydrolyzed biomass before the step of emulsifying.

The method may further comprise drying the liquid emulsion. The method may also further comprise storing the dried emulsion. The emulsion may be dried by membrane filter press drying, drying, fluidized bed drying, lyophilization, freeze drying, tray drying, vacuum tray drying, drum drying, vacuum mixer/reactor drying, excipient drying, solvent drying, fluidized spray drying, conveyer drying, ultrafiltration, evaporation, osmotic dehydration, freezing, absorbent addition, extrusion or a combination thereof. The emulsion may be dried by a method of spray-drying, fluidized spray drying, conveyer drying or combinations thereof. In these embodiments, the emulsion may be extruded. In these embodiments, the method may further comprise adding an ingredient to the hydrolysate. The ingredient may be flavors, flavor enhancers, sweeteners, pigments, vitamins, minerals, pre-biotic compounds, pro-biotic compounds, therapeutic ingredients, medicinal ingredients, functional food ingredients, food ingredients, processing ingredients, or combinations thereof.

In some embodiments of the method, the method may further comprise the step of pretreating the biomass. The pretreating may be pasteurization, heat shocking, washing, adding antioxidants, pH adjusting, adding omega-3 fatty acids, shearing/cell weakening or combinations thereof.

In some embodiments of the method, the biomass is previously dried and reconstituted. In other embodiments of the method, the biomass is in a fermentation broth.

The invention further provides a stable emulsion comprising an emulsified hydrolyzed biomass. The invention also provides products comprising the stable emulsion, including a food product comprising the stable emulsion, a nutritional product comprising the stable emulsion, and a pharmaceutical product comprising the stable emulsion The invention also provides a dry composition produced by drying the stable emulsion. The step of drying may be membrane filter press drying, spray drying, fluidized bed drying, lyophilization, freeze drying, tray drying, vacuum tray drying, drum drying, vacuum mixer/reactor drying, excipient drying, solvent drying, fluidized spray drying, conveyer drying, ultrafiltration, evaporation, osmotic dehydration, freezing, absorbent addition, extrusion or a combination thereof.

In some embodiments, the stable emulsion is extruded.

The invention also provides the stable emulsion further comprising a stabilization agent. The stabilization agent may be microencapsulants, surfactants, emulsion stabilizers or a combination thereof.

In some embodiments of stable emulsion, the biomass is hydrolyzed by a method of enzymatic hydrolysis, chemical disruption, physical-mechanical disruption, physical-nonmechanical disruption or combinations thereof. The enzymatic hydrolysis may be conducted with xylanases, cellulases, amylases, carbohydrases, proteases, chitinases, or a combination thereof.

In some embodiments of stable emulsion, the hydrolysate is emulsified by mechanical agitation, ultrasonic vibration, heating, or a combination thereof. The mechanical agitation may comprise homogenization.

In some embodiments, the biomass comprises a microorganism which may be algae, protists, bacteria or fungi. The microorganism may be an oleaginous microorganism. The microorganism may be microorganisms of the genus *Thraustochytrium*, microorganisms of the genus *Schizochytrium*, microorganisms of the genus *Althornia*, microorganisms of the genus *Aplanochytrium*, microorganisms of the genus *Japonochytrium*, microorganisms of the genus *Elina*, microorganisms of the genus *Crypthecodinium*, microorganisms of the genus *Mortierella* or mixtures thereof.

In some embodiments of the stable emulsion, the biomass is derived from a plant source. In some embodiments, the plant source has been genetically modified to produce long chain polyunsaturated fatty acids, and the plant may be soybean, corn, safflower, sunflower, canola, flax, peanut, mustard, rapeseed, chickpea, cotton, lentil, white clover, olive, palm, borage, evening primrose, linseed or tobacco. In other embodiments, the plant source has not been genetically modified to produce long chain polyunsaturated fatty acids, and the plant may be soybean, corn, safflower, sunflower, canola, flax, peanut, mustard, rapeseed, chickpea, cotton, lentil, white clover, olive, palm, borage, evening primrose, linseed or tobacco.

In some embodiments of the stable emulsion, the biomass is derived from an animal source. The animal source may be aquatic animals, animal tissues or animal products.

In some embodiments, the stable emulsion comprises an LC PUFA. In some embodiments, the LC PUFA has a carbon chain length of at least 18. In some embodiments, the LC PUFA has a carbon chain length of at least 22. In some embodiments, the LC PUFA has at least three double bonds. In other embodiments, the LC PUFA has at least four double bonds. In some embodiments, the LC PUFA is docosahexaenoic acid, docosapentaenoic acid, arachidonic acid, eicosapentaenoic acid, or gamma-linolenic acid.

In some embodiments, the stable emulsion is more stable than the hydrolyzed biomass before it was emulsified.

In some embodiments, the stable emulsion further comprises an additional ingredient. The additional ingredient may be flavors, flavor enhancers, sweeteners, pigments, vitamins, minerals, pre-biotic compounds, pro-biotic compounds, therapeutic ingredients, medicinal ingredients, functional food ingredients, food ingredients, processing ingredients, or combinations thereof.

In some embodiments of the stable emulsion, the biomass is pretreated before being emulsified and hydrolyzed. The step of pretreating may be pasteurization, heat shocking, washing, adding antioxidants, pH adjusting, adding omega-3 fatty acids, shearing/cell weakening or combinations thereof. In some embodiments, the step of pretreating comprises drying and reconstituting the biomass.

The invention also provides a nutritional supplement comprising the stable emulsion. The supplement may be in the form of a tablet. The supplement may comprise a multivitamin. In some embodiments of the nutritional supplement, the stable emulsion is dried. In this embodiment, the supplement may be in the form of a tablet, and the supplement may comprise a multivitamin.

The present invention further provides a medicinal product comprising the stable emulsion. In some embodiments, the stable emulsion is dried.

The invention further provides a stable emulsion useful in an infant formula product comprising an emulsified hydrolyzed biomass, in which the biomass comprises docosahexaenoic acid and arachidonic acid in a ratio of from about 1:0.5 to about 1:5. In some embodiments the docosahexaenoic acid and arachidonic acid are in a ratio of about 1:1.5. In other embodiments the docosahexaenoic acid and arachidonic acid are in a ratio of about 1:2.

Also included in the present invention is an infant formula product comprising the stable emulsion. In some embodiments, the infant formula product contains a biomass comprising docosahexaenoic acid and arachidonic acid in a ratio of about 1:1.5. In other embodiments, the infant formula product contains a biomass comprising docosahexaenoic acid and arachidonic acid in a ratio of about 1:2.

In some embodiments, the infant formula product is dried. In some embodiments, the dried infant formula product, upon addition of liquid according to instructions, results in a product that will have an ARA content of from about 0.5% to about 0.6% of its fatty acid content and/or a DHA content of from about 0.15% to about 0.36% of its fatty acid content. In some embodiments, the infant formula product is liquid. In some embodiments, the liquid infant formula product has an ARA content of from about 0.5% to about 0.6% of its fatty acid content and/or a DHA content of from about 0.15% to about 0.36% of its fatty acid content.

The invention further provides a method for producing a product comprising a nutrient. The method includes hydrolyzing a biomass comprising the nutrient to produce a hydrolyzed biomass, emulsifying the hydrolyzed biomass to form a stable product, and storing the stable product. In some embodiments, the step of storing is conducted under a condition of cold temperatures, non-oxidizing conditions and/or absence of light. In some embodiments, the method further comprises processing the stable product after the step of storing. Processing of the stable product includes extraction, fractionation or purification.

DESCRIPTION OF THE INVENTION

The nutritional, cosmetic and pharmaceutical product compositions and methods for preparation of the same, as taught by the present invention, provide for increased intake of nutrients, particularly LC PUFAs, particularly omega-3 and omega-6 LC PUFAs. This improvement can provide health benefits to those consuming such products. The present invention also provides methods to minimize the oxidative degradation of nutrients, including LC PUFAs, in the products of the present invention. The present invention is directed in part towards a stable, palatable composition comprising an emulsified biomass hydrolysate for use in, or as a nutritional (including nutraceutical) product, a cosmetic product, and/or a pharmaceutical product (medicinal and/or therapeutic). This composition can be a liquid emulsion or a dry composition. The invention also includes use of compositions of the invention as delivery systems or carriers for bioactive or therapeutic compounds, which can occur naturally in the biomass or be added to it. Biomass sources can include microbial, plant and animal sources. The methods and products of the invention are especially advantageous when the biomass is derived from a source that produces or comprises beneficial nutrients, including LC PUFAs.

Nutrients including LC PUFAs are susceptible to oxidative degradation and the emulsification process of the present invention helps to protect the nutrients and/or LC PUFAs from the unfavorable conditions that contribute to their degradation. The present inventors have surprisingly discovered that the emulsified products that are formed as a result of the methods of the present invention are quite stable. Without being bound by theory, the present inventors believe that the hydrolyzed biomass itself serves as a microencapsulant, emulsion stabilizer, and oxidative stabilizer as a result of the particulates present in the biomass such as, for example, cell membrane fragments, nuclei fragments, and other intracellular components, becoming layered on the oil/water interface in the emulsion. When the emulsified biomass hydrolysate is dried, the particulates surround the oil droplets and continue to act as a microencapsulent, as well as possibly providing a physical barrier to oxidation or oxidation catalytic compounds, such as oxygen, free radical compounds, and metals. Therefore, the present inventors have surprisingly discovered that the use of added surfactants, emulsion stabilizers and/or microencapsulants, although not precluded from inclusion in the compositions of the present invention, are not required to form a stable emulsion or a dry composition, such as a powder, that results, e.g., from drying of the emulsion. The present inventors have found that emulsified biomass products of the present invention preferably exhibit favorable organoleptic properties and can be incorporated into various nutritional, cosmetic and pharmaceutical products without imparting an unpleasant taste or odor.

In a first embodiment, the present invention includes a method for producing a stable product comprising a nutrient. This method includes the step of hydrolyzing a nutrient-containing biomass to produce a hydrolyzed biomass, and emulsifying the hydrolyzed biomass to form a stable product. The stable product is typically an emulsion or a dry composition resulting from subsequent drying of the emulsion. An emulsion is typically a heterogenous system comprising at least one immiscible liquid (known as the dispersed phase, internal phase or discontinuous phase) intimately dispersed in another liquid (known as the dispersion medium, external phase or continuous phase) in the form of globules or droplets, whose diameters can be in the nano, micro or millimeter range (dispersed phase globules generally have a diameter in the range of about 0.01 to 10 microns, though some as small as 0.001 microns and as large as 100 microns are known). Ordinarily emulsions are made up of a polar and a nonpolar component, each of which is a liquid. When the dispersed phase is non-polar (oil) and the external phase is polar (water), the emulsion is known as an oil-in-water emulsion. When the dispersed phase is water and the dispersion medium is oil, the emulsion is of the water-in-oil kind. Water-in-oil emulsions are ordinarily insoluble in water, not water-washable, will absorb water, and may be "greasy." Butter and margarine are examples of water-in-oil emulsions, and typically have a lipid content of between about 80% by weight and about 95% by weight. Oil-in-water emulsions are miscible with water, are water washable, will absorb water, and are nongreasy. The emulsions of the present invention can be either type of emulsion, and the proper type of emulsion and appropriate moisture level of the emulsion may readily be determined by one skilled in the art depending on a number of relevant factors, including the starting material and the type of product desired, and the eventual use of that product. In many embodiments, a preferred emulsion is an oil-in-water emulsion. An emulsion produced by the processes of the present invention is typically of an oil-in-water type, although further processing (i.e., partial dehydration) may convert such emulsions to a water-in-oil emulsion. The emulsion of the present invention may be a nano, micro or macroemulsion. Some nano and microemulsions can be thermodynamically stable. An emulsion can also refer to a suspension of at least one immiscible solid immersed in a liquid. Such solids can include solid lipids or biomass. As used herein, the phrase "emulsion of the present invention" refers to a biomass hydrolysate that has undergone emulsification and has a water content of between about 30% and about 99%. The phrase "dry composition of the present invention" refers to a composition that results from drying the emulsion of the present invention and has a water content of between about 1% and about 30%. As discussed below, in a preferred embodiment, the emulsifying agent(s) can be products of the biomass hydrolysate.

A nutrient contained by a biomass of the present invention can comprise any nutrient or combination of nutrients. In one embodiment, the nutrient is a protein. Particularly preferred proteins include functional proteins such as peptides and glycoproteins. In another embodiment, preferred nutrients include an isoflavone, a flavonoid, a phytochemical, an antioxidant, a lutein, a lycopene, and a saponin. In another preferred embodiment, the nutrient can comprise a lipid. A preferred lipid includes an acylglycerol, a phosphoglyceride, a free fatty acid (including, but not limited to a polyenoic fatty acid), a fatty acid ester, a sphingolipid, a ganglioside, a phospholipid (including lecithin, phoshphatidylserine and phosphatidylcholine), a glycolipid, a wax, a tocopherol, a tocotrienol, a sterol and/or a sterol ester, a carotenoid, a xanthophyll (e.g., oxycarotenoids), a pigment, a polyphenol, a hydrocarbon, an antioxidant, an isoprenoid-derived compound and/or a combination of these compounds. More preferred lipids include triacylglycerols and phosphoglycerides.

A preferred lipid in methods of the present invention is a polyunsaturated fatty acid (PUFA). Preferred PUFAs of the present invention include C18, C20, C22, or C24 omega-3 or omega-6 PUFAs. Preferably, the PUFA is a long chain PUFA (LC PUFA), i.e., having 20 or more carbons, more preferably comprising a C20 or C22 omega-3, or a C20 or C22 omega-6 polyunsaturated fatty acid. A preferred C18 PUFA is gamma-linolenic acid (GLA). An LC PUFA of the present invention contains at least two double bonds and preferably, three double bonds, and even more preferably at least four double bonds. PUFAs having 4 or more unsaturated carbon-carbon bonds are also commonly referred to as highly unsaturated fatty acids, or HUFAs. In particular, the LC PUFA includes docosahexaenoic acid (at least about 10, about 20, about 30, about 40, about 50 or about 60 percent of dry weight and/or at least about 10, about 20, about 30, about 40, about 50, about 60, about 70 or about 80 weight percent of total fatty acids), docosapentaenoic acid, n-3 and/or n-6, (at least about 5, about 10, about 15, about 20, about 30, about 40, about 50 or about 60 percent of dry weight and/or at least about 10, about 20, about 30, about 40, about 50, about 60, about 70 or about 80 weight percent of total fatty acids), arachidonic acid (at least about 10, about 20, about 30, about 40, about 50 or about 60 percent of dry weight and/or at least about 10, about 20, about 30, about 40, about 50, about 60, about 70 or about 80 weight percent of total fatty acids) and/or eicosapentaenoic acid (at least about 10, about 20, about 30, about 40, or about 50 percent of dry weight and/or at least about 10, about 20, about 30, about 40, about 50, about 60, about 70 or about 80 weight percent of total fatty acids). The PUFAs can be in any of the common forms found in natural lipids including but not limited to triacylglycerols, diacylglycerols, monoacylglycerols, phospholipids, free fatty acids, esterified fatty acids, or in natural or synthetic derivative forms of these fatty acids (e.g. calcium salts of fatty acids, ethyl esters, etc). The term LC PUFA, as used in the present invention, can refer to either an oil comprising a single omega-3 LC PUFA such as DHA, an oil comprising a single omega-6 LC PUFA such as ARA or DPA n-6, or an oil comprising a mixture of two or more LC PUFAs such as DHA, DPA n-6, ARA, and EPA. In preferred embodiments, the product comprises an LC PUFA in combination with at least one other nutrient. An advantage of the present invention is that use of the hydrolyzed biomass product allows for at least a significant portion of the nutrients originally present in the biomass to be incorporated into the product. Accordingly, in preferred embodiments the present invention includes a product that incorporates a combination of nutrients, and in most preferred embodiments, the combination of nutrients includes at least one LC PUFA.

A preferred biomass source of nutrients, including LC PUFAs, in the compositions and methods of the present invention includes a microbial source. Microbial sources and methods for growing microorganisms comprising nutrients and/or LC PUFAs are known in the art (*Industrial Microbiology and Biotechnology*, $2^{nd}$ edition, 1999, American Society for Microbiology). Preferably, the microorganisms are cultured in a fermentation medium in a fermentor. Thus, the biomass can be a fermentation broth or a dried fermentation biomass that has been reconstituted. A fermentation broth can include a washed broth, i.e., one in which water is added to a fermentation broth comprising microorganisms, the broth is mixed and the mixture is concentrated. The methods and compositions of the present invention are applicable to any microorganism that produces any kind of nutrient or desired component such as, for example algae, protists, bacteria and fungi (including yeast).

If the desired nutrient is an LC PUFA, microbial sources can include a microorganism such as an algae, bacteria, fungi and/or protist. Preferred organisms include those selected from the group consisting of golden algae (such as microorganisms of the kingdom Stramenopiles), green algae, diatoms, dinoflagellates (such as microorganisms of the order Dinophyceae including members of the genus *Crypthecodinium* such as, for example, *Crypthecodinium cohnii*), yeast, and fungi of the genera *Mucor* and *Mortierella*, including but not limited to *Mortierella alpina* and *Mortierella* sect. *schmuckeri*. Members of the microbial group Stramenopiles include microalgae and algae-like microorganisms, including the following groups of microorganisms: Hamatores, Proteromonads, Opalines, Develpayella, Diplophrys, Labrinthulids, Thraustochytrids, Biosecids, Oomycetes, Hypochytridiomycetes, Commation, Reticulosphaera, Pelagomonas, Pelagococcus, Ollicola, Aureococcus, Parmales, Diatoms, Xanthophytes, Phaeophytes (brown algae), Eustigmatophytes, Raphidophytes, Synurids, Axodines (including Rhizochromulinaales, Pedinellales, Dictyochales), Chrysomeridales, Sarcinochrysidales, Hydrurales, Hibberdiales, and Chromulinales. While processes of the present invention can be used to produce forms of nutrients that can be produced in a wide variety of microorganisms, for the sake of brevity, convenience and illustration, this detailed description of the invention will discuss processes for growing microorganisms which are capable of producing lipids comprising omega-3 and/or omega-6 polyunsaturated fatty acids, in particular microorganisms that are capable of producing DHA (or closely related compounds such as DPA, EPA or ARA). Additional preferred microorganisms are algae, such as Thraustochytrids of the order Thraustochytriales, more specifically Thraustochytriales, including *Thraustochytrium, Schizochytrium* and *Ulkenia*, and including Thraustochytriales which are disclosed in commonly assigned U.S. Pat. Nos. 5,340,594 and 5,340,742, both issued to Barclay, all of which are incorporated herein by reference in their entirety, in addition to microorganisms of the genus *Althornia*, genus *Aplanochytrium*, genus *Japonochytrium*, and genus *Elina* and mixtures thereof. More preferably, the microorganisms are selected from the group consisting of microorganisms having the identifying characteristics of ATCC number 20888, ATCC number 20889, ATCC number 20890, ATCC number 20891 and ATCC number 20892, strains of *Mortierella schmuckeri* and *Mortierella alpina*, strains of *Crypthecodinium cohnii*, mutant strains derived from any of the foregoing, and mixtures thereof. It should be noted that many experts agree that *Ulkenia* is not a separate genus from the genus *Thraustochytrium*. Accordingly, as used herein, the genus *Thraustochytrium* will include *Ulkenia*. Oleaginous microorganisms are also preferred. As used herein, "oleaginous microorganisms" are defined as microorganisms capable of accumulating greater than 20% of the dry weight of their cells in the form of lipids. Genetically modified microorganisms that produce LC PUFAs are also suitable for the present invention. These can include naturally LC PUFA-producing microorganisms that have been genetically modified as well as microorganisms that do not naturally produce LC PUFAs (including yeasts, bacteria, fungi, algae and/or protists) but that have been genetically engineered to do so.

Suitable organisms may be obtained from a number of available sources, including by collection from the natural environment. For example, the American Type Culture Collection currently lists many publicly available strains of microorganisms identified above. As used herein, any organism, or any specific type of organism, includes wild strains, mutants, or recombinant types. Growth conditions in which to culture or grow these organisms are known in the art, and appropriate growth conditions for at least some of these organisms are disclosed in, for example, U.S. Pat. No. 5,130,242, U.S. Pat. No. 5,407,957, U.S. Pat. No. 5,397,591, U.S. Pat. No. 5,492,938, and U.S. Pat. No. 5,711,983, all of which are incorporated herein by reference in their entirety.

A microbial biomass comprising a nutrient can refer to a biomass that has not been separated from the culture media in which the biomass organism was cultured. An example of a culture media is a fermentation broth. In one embodiment, the biomass is separated from its culture media by a solid/liquid separation prior to treatment by methods of the present invention. Typical solid/liquid separation techniques include centrifugation, filtration, and membrane filter pressing (plate and frame filter press with squeezing membranes). This (harvested) biomass usually has a dry matter content varying between 5% and 60%. If the water content is too high, the biomass may be dewatered by any method, such as, for example, spray drying, fluidized bed drying, lyophilization, freeze drying, tray drying, vacuum tray drying, drum drying, solvent drying, excipient drying, vacuum mixer/reactor drying, drying using spray bed drying, fluidized spray drying, conveyor drying, ultrafiltration, evaporation, osmotic dehydration, freezing, extrusion, absorbent addition or other methods, or combinations thereof. The drying techniques referenced herein are well known in the art. For example, excipient drying refers to the process of atomizing liquids onto a bed of material such as starch and solvent drying refers to a process where a solvent, miscible with water, is used in excess to replace the water. The biomass may optionally be washed in order to reduce extracellular components. In preferred embodiments, the biomass may have up to about 99% moisture by weight before being treated by any methods of the present invention. Preferably, the moisture content is between about 50% and about 99%, more preferably between about 65% and about 85%. The fermentation broth may be dried, optionally frozen, and then reconstituted to a moisture content of any desired level before treatment by any of the methods of the present invention. Alternatively, hydrolyzing enzymes may be applied to dried or semi-dried biomass having a moisture lower than 50%.

Another preferred biomass source of nutrients, including LC PUFAs, in the compositions and methods of the present invention includes a plant source, such as oilseed plants. Since plants do not naturally produce LC PUFAs, plants producing LC PUFAs are those genetically engineered to express genes that produce LC PUFAs. Such genes can include genes encoding proteins involved in the classical fatty acid synthase pathways, or genes encoding proteins involved in the PUFA polyketide synthase (PKS) pathway. The genes and proteins involved in the classical fatty acid synthase pathways, and genetically modified organisms, such as plants, transformed with such genes, are described, for example, in Napier and Sayanova, *Proceedings of the Nutrition Society* (2005), 64:387-393; Robert et al., *Functional Plant Biology* (2005) 32:473-479; or U.S. Patent Application Publication 2004/0172682. The PUFA PKS pathway, genes and proteins included in this pathway, and genetically modified microorganisms and plants transformed with such genes for the expression and production of PUFAs are described in detail in: U.S. Pat. No. 6,566,583; U.S. Patent Application Publication No. 20020194641, U.S. Patent Application Publication No. 20040235127A1, and U.S. Patent Application Publication No. 20050100995A1, each of which is incorporated herein by reference in its entirety.

Preferred oilseed crops include soybeans, corn, safflower, sunflower, canola, flax, peanut, mustard, rapeseed, chickpea, cotton, lentil, white clover, olive, palm oil, borage, evening primrose, linseed, and tobacco that have been genetically modified to produce LC PUFA as described above.

Genetic transformation techniques for microorganisms and plants are well-known in the art. Transformation techniques for microorganisms are well known in the art and are discussed, for example, in Sambrook et al., 1989, *Molecular Cloning: A Laboratory Manual*, Cold Spring Harbor Labs Press. A general technique for transformation of dinoflagellates, which can be adapted for use with *Crypthecodinium cohnii*, is described in detail in Lohuis and Miller, *The Plant Journal* (1998) 13(3): 427-435. A general technique for genetic transformation of Thraustochytrids is described in detail in U.S. Patent Application Publication No. 20030166207, published Sep. 4, 2003. Methods for the genetic engineering of plants are also well known in the art. For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R.

and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119. See also, Horsch et al., *Science* 227:1229 (1985); Kado, C. I., *Crit. Rev. Plant. Sci.* 10:1 (1991); Moloney et al., *Plant Cell Reports* 8:238 (1989); U.S. Pat. No. 4,940,838; U.S. Pat. No. 5,464,763; Sanford et al., *Part. Sci. Technol.* 5:27 (1987); Sanford, J. C., *Trends Biotech.* 6:299 (1988); Sanford, J. C., *Physiol. Plant* 79:206 (1990); Klein et al., *Biotechnology* 10:268 (1992); Zhang et al., *Bio/Technology* 9:996 (1991); Deshayes et al., *EMBO J,* 4:2731 (1985); Christou et al., *Proc Natl. Acad. Sci. USA* 84:3962 (1987); Hain et al., *Mol. Gen. Genet.* 199:161 (1985); Draper et al., *Plant Cell Physiol.* 23:451 (1982); Donn et al., In Abstracts of VIIth International Congress on Plant Cell and Tissue Culture IAPTC, A2-38, p. 53 (1990); D'Halluin et al., *Plant Cell* 4:1495-1505 (1992) and Spencer et al., *Plant Mol. Biol.* 24:51-61 (1994).

When oilseed plants are the source of LC PUFAs, the seeds can be harvested and processed to remove any impurities, debris or indigestible portions from the harvested seeds prior to subjecting them to a step of hydrolyzing. Processing steps vary depending on the type of oilseed. Processing steps can include threshing (such as, for example, when soybean seeds are separated from the pods), dehulling (removing the dry outer covering, or husk, of a fruit, seed, or nut), drying, cleaning, grinding, milling and flaking. After the seeds have been processed to remove any impurities, debris or indigestible materials, they can be added to an aqueous solution, preferably water, and then mixed to produce a slurry. Preferably, milling, crushing or flaking is performed prior to mixing with water. A slurry produced in this manner can be treated and processed the same way as described for a microbial fermentation broth. Size reduction, heat treatment, pH adjustment, pasteurization and other treatments can be used in order to improve hydrolysis, emulsion preparation, and quality (nutritional and sensory).

Another preferred biomass source of nutrients, including LC PUFAs, in the compositions and methods of the present invention includes an animal source. Examples of animal sources include aquatic animals (e.g., fish, marine mammals, and crustaceans such as krill and other euphausids) and animal tissues comprising lipids (e.g., brain, liver, eyes, etc.) and animal products such as eggs or milk. For example, fish, especially underutilized species, can be used as a starting material to produce a hydrolysate emulsion of the present invention that could be used as is or dried to produce microencapsulated powder using microencapsulation techniques, such as spray drying, cold dehydration processes, pan coating, fluid bed coating, co-extrusion processes, emulsion evaporation, evaporative dispersion processes, spinning disk processes, coacervation processes, and inclusion complexation. The hydrolysate would be a good source of omega-3 oils and proteins/amino-acids. Fish meal or fish flour production is a known process. In this invention, enzymes can be added in the process of producing fish meal or fish flour to promote cell disruption. For example, dried fish can be milled to produce a flour, reconstituted in water and enzymes added for cell disruption. As will be appreciated by those in the art, organisms other than fish can be employed to produce meals and flours, such as krill.

After hydrolysis, ingredients that improve microencapsulation, and/or quality, and/or stability can be added to produce a stable emulsion with good nutritional and organoleptic quality. The emulsion could be subjected to drying to produce a powder that could be used in food or feed applications. The biomass hydrolyzate may be modified to alter its composition by either extracting/removing selected components or adding selected components to enhance the product quality, appearance, sensory and nutritional value. For example, components can be removed from the hydrolyzate that could cause degradation of the nutrient(s) in the hydrolyzate after an emulsion is formed (e.g., pro-oxidant metals, such as iron, copper, or nickel, lipoxidase enzymes, or free radicals) or that could have a negative impact on the final product (e.g., bad tasting components). The type of material added could be based on a targeted or preferred composition of the final product including lipid profile, protein profile, carbohydrate profile or other compounds that can enhance nutritional or therapeutic value of the final product. Additional components such as antioxidants, pH adjustors and/or different biomass sources may be added to a biomass source prior to hydrolysis to produce a modified biomass. In addition, lipids in a biomass hydrolysate can be removed or reduced by extraction (such as solvent extraction) or other separation methods to produce a defatted hydrolysate product and an extracted lipid product. The defatted hydrolysate product can be desolventized and dried as needed. It can then be used as is in food or feed applications or could be further processed (purified, extracted, modified, etc.) for the generation of value added products. The extracted lipid product can be used as a lipid source in a variety of applications.

Alternatively, other fats may be added to enrich or alter the composition of the final product. For instance, if a source is lacking the essential fatty acid EPA, e.g., *Crypthecodinium*, another source of EPA (e.g., microbial, genetically engineered seeds, fish oil) could be added to a *Crypthecodinium* fermentation broth before or after hydrolysis in order to produce a final product that contains EPA. Further, an infant formula product or intermediate product could be produced using this technology by balancing the components of the product prior to drying. The lipid profile, for example, could be balanced to mimic breast milk. Minerals, proteins and other components can likewise be added to or removed from (using ultrafiltration, reverse osmosis or other methods) the biomass. In similar fashion, proteins, peptides, carbohydrates, and other components can be added to or removed from the biomass. The biomass may undergo optional pre-treatment steps including pasteurization, heat shocking, washing, adding antioxidants, pH adjusting, adding omega-3 fatty acids, shearing/cell weakening and any combination thereof. In one embodiment, the biomass may be pasteurized either prior to or during the methods of the present invention. With advances in health and nutrition, the technology could be used to produce products meeting present and future composition requirements for both general and specific health and nutrition needs.

As noted above, a particular application of the present invention is a product that mimics the lipid profile of human breast milk. Typically, human breast milk contains from about 0.5% to about 0.6% of its fatty acid content as ARA, and from about 0.15% to about 0.36% of its fatty acid content as DHA. Thus, preferred ratios of DHA:ARA in products of the present invention useful for infant formula are from about 1:0.5 to about 1:5. Additional preferred ratios are at about 1:1.5, at about 1:2 and at about 1:3. Further embodiments of the present invention include infant formula products comprising products of the present invention having DHA:ARA ratios as described above. Such infant formula products can either be dried or liquid. If dried, such infant formula products can be formulated such that, upon addition of liquid according to instructions, the resulting product will have an ARA content of from about 0.5% to about 0.6% of its fatty acid content and/or a DHA content of from about 0.15% to about 0.36% of its fatty acid content. If liquid, such infant formula products will have an ARA content of from about 0.5% to about 0.6% of its fatty acid content and/or a DHA content of from about 0.15% to about 0.36% of its fatty acid content.

Preferably, where the biomass is a microbial biomass, pasteurization is employed after the fermentation is complete, but before further processing of the fermentation broth. The benefits of pasteurization for microorganism sources include preventing exposure of a production organism to the environment and inactivating unwanted enzymatic activities. Depending on the species of the production organism, pasteurization is performed at temperatures of from about 60° C. to about 100° C. Pasteurization may be accomplished using direct or indirect methods. For example, the pasteurization may be accomplished by heating directly with steam into the liquid or broth or indirectly, through heat exchangers. The following preferred pasteurization conditions may be employed, especially for organisms of the genera *Schizochytrium, Thraustochytrium, Mortierella* and *Crypthecodinium*. The fermentation broth is suitably pasteurized at from about 50° C. to about 95° C., preferably from about 60° C. to about 90° C., and more preferably from about 65° C. to about 85° C. In a batch pasteurization process, pasteurization may take place for between about 30 and about 90 minutes, preferably from about 50 to about 75 minutes, and optimally, from about 55 to about 65 minutes, and can be performed by any suitable heating means. Preferably, the broth may be cooled or allowed to cool after pasteurization, to about 25° C., before further processing. In a continuous High Temperature Short Time (HTST) process, the pasteurization time can vary from about 15 seconds to about 5 minutes. Pasteurization temperatures for HTST processes will be at the upper end of acceptable temperatures, typically above about 80° C. Prior to pasteurization, a deaeration step to remove entrained bubbles and lower the dissolved oxygen concentration may also be desirable or necessary. This can be performed by any suitable deaeration means. In another embodiment, the biomass may be washed as a pretreatment method. Washing, as described here, is the removal of unwanted compounds generated by the process of fermentation. This can be achieved, for example, by dilution with water and centrifugation. Other methods such as ultrafiltration, difiltration or reverse osmosis could be used to concentrate and remove nondesirable soluble compounds. Dilution rates will vary depending upon removal efficiency desired, cost to remove undesirables, capacity rates for processing equipment, post-handling of undesirables, etc. In another embodiment, the broth/biomass may be pH adjusted with buffers, acids or bases to obtain a desired pH. For example, this pretreatment method could be used to aid downstream processing steps such as hydrolysis, enzymatic hydrolysis, and/or drying steps. This pretreatment method could also be used to aid the alteration of biomass/broth components such as component solubility, complexation, charge status and chemical reaction.

Optionally, an antioxidant may be added to the biomass before subjecting the same to the processes of the present invention, or at any point during the process. Such an antioxidant may help preserve the resulting products. The oxidative state and stability of a nutrient including a lipid may be measured in a number of ways, and descriptions of many of these techniques are available from the American Oil Chemist's Society, as well as from other sources. Suitable antioxidants may be chosen by the skilled artisan. Preferred antioxidants include ascorbyl palmitate, tocopherols, citric acid, ascorbic acid, tertiary butyl hydroquinone (TBHQ), rosemary extract, lecithin, and mixtures thereof. Particularly preferred antioxidants include a mixture of (a) ascorbic acid, (b) ascorbyl palmitate and (c) a tocopherol, added at effective concentrations. Preferred concentrations for these antioxidants include: from about 0.2% to about 5% ascorbic acid, from about 0.1% to about 1% ascorbyl palmitate, and from about 0.1% to about 1% tocopherol.

Optional pretreatment methods include a pretreatment designed to weaken and/or shear the cell walls or membranes of the biomass source, if applicable, before the hydrolysis and/or emulsion step. Such pretreatments include, for example, grinding, pre-milling, homogenization at low pressures, and shear mixing. These pretreatments are typically carried out under more mild conditions than treatments that are designed to more completely destroy the integrity of cell walls and/or membranes. In some embodiments, pretreatment steps, and other steps before hydrolysis such as biomass recovery steps, can be conducted in a protective atmosphere (e.g. nitrogen) so as to limit contact of the product with oxygen which could cause degradation of the nutrient in the event that the nutrient is sensitive to oxidative degradation, such as LC PUFAs. Pretreatments and pretreatment conditions may be determined by one of skill in the art to achieve the desired result.

Methods of hydrolyzing a biomass may include those known in the art. Hydrolysis refers to any type of cell disruption, i.e., any method where the integrity of the cell is broken and the contents of such cell may be released, and in particular refers to "wet cell" lysis methods. Use of any of the terms "hydrolysis", "cell disruption", and/or "cell lysis", all refer to the process of breaking the integrity of a cell. Hydrolysis methods include any method to disrupt cells and/or break open cell walls and include, for example, methods such as enzymatic hydrolysis, chemical disruption of cells through the use of bases, acids, detergents or solvents; physical-mechanical cell disruption through the use of ultrasonication, wet milling, high pressure homogenization, impingement, and/or pressure extrusion; and/or physical-non-mechanical means such as osmotic shock, freeze-thawing, drying and/or steam treatment. Such methods will be optimized to result in cell breakage. For example, if a homogenization step is used to effect hydrolysis, the homogenization step will preferentially be conducted by a high pressure homogenizer. For example, a "knife-edge" type valve for a high pressure homogenizer is preferred for cell breakage. In a further embodiment, the hydrolysis step can be conducted in a protective atmosphere (e.g. nitrogen) so as to limit contact of the product with oxygen which could cause degradation of the nutrient in the event that the nutrient is sensitive to oxidative degradation, such as LC PUFAs. An appropriate method may be determined by one of skill in the art based on the type of organism, fermentation conditions, type of nutrient, and so on.

In a preferred embodiment, methods of enzymatic hydrolysis are used, preferentially hydrolysis by the addition of enzymes to a biomass rather than by autolysis. The inventors have found that surprisingly, such use of exogenous enzyme hydrolysis improves the taste qualities of the resultant product. For different biomass sources, different enzymes and reaction conditions can be employed. An important enzyme selection criterion is to select an enzyme that will attack and degrade a portion of the material in the membrane (such as the proteins, polysaccharides, cell outer membrane, peptidoglycan layer, cellulose, chitin, hemicellulose, lignin, lignin-related compounds, and other cell wall components).

In addition, it is important that any enzyme selected for hydrolysis does not hydrolyze the nutrient (e.g., LC PUFAs) or otherwise cause it to be unstable or be reduced in value. In this embodiment, the use of an enzyme is intended to promote hydrolysis of the biomass and not modify the nutrient. Non-specific protease enzymes such as trypsin, chymotrypsin, or the like are used to degrade protein components of cells and carbohydrase enzymes such as amylase can be used to degrade carbohydrate components. The selection of reaction conditions, including enzyme type, enzyme concentration, temperature, pH, water activity, other reagent concentration, reaction time, etc. will depend in part on the specific enzyme and material within the cell membrane. These conditions can be readily determined from information about the enzyme (and typically available from the supplier or in the literature), or determined by someone skilled in the art. Examples of enzymes that can be used to hydrolyze biomass include carbohydrases such as xylanases, cellulases (such as CELLUCLAST 1.5 L™ (Ekozyme, Bagsvaerd, Denmark)), amylases (such as TERMAMYL™ (Ekozyme, Bagsvaerd, Denmark)), glucoamylases and alpha amylases (such as VISCOZYME™); proteases (such as ALCALASE™ (Novozyme, Bagsvaerd, Denmark)); lipases; chitinases; chitosanases; glucanases; α-glucanases, such as NOVOZYM 234 (Novozyme); β-glucanases such as laminarinases; and combinations thereof. Surfactants may be added to the enzymes to allow for greater efficiency. Enzymes that also lyse cells, but are designed for flavor or other purposes (such as FLAVOURZYME® (Novozymes, Bagsvaerd, Denmark)) can be used for cell breakage and/or flavor improvement. Processes for the enzyme treatment of biomass for the recovery of lipids are disclosed in U.S. Provisional Patent Application No. 60/377,550, entitled "HIGH-QUALITY LIPIDS AND METHODS FOR PRODUCING BY ENZYMATIC LIBERATION FROM BIOMASS," filed on May 3, 2002; PCT Patent Application Serial No. PCT/US03/14177 entitled "HIGH-QUALITY LIPIDS AND METHODS FOR PRODUCING BY ENZYMATIC LIBERATION FROM BIOMASS," filed on May 5, 2003; and copending U.S. patent application Ser. No. 10/971,723, entitled "HIGH-QUALITY LIPIDS AND METHODS FOR PRODUCING BY LIBERATION FROM BIOMASS," filed on Oct. 22, 2004, the disclosures of which are hereby incorporated by reference herein in their entirety. The enzyme or combination of enzymes used to hydrolyze the biomass will depend largely on the cell wall/cell membrane composition of the specific biomass. One of skill in the art could readily identify appropriate enzymes to hydrolyze a selected biomass. Multiple cell disruption methods may be utilized. For example, mechanical cell disruption may be performed prior to enzymatic hydrolysis, or vice versa.

Microorganisms, plant sources such as seeds, and animal sources are known sources from which to extract lipids. However, when enzymatic hydrolysis is employed in combination with surfactants to liberate the lipids from, for example, a microorganism, prior to extraction, an unstable emulsion may result. This emulsion is viewed as a nuisance to the extraction process because it interferes with the separation and recovery of purified or partially purified lipids. In contrast, the inventors of the present invention have found that a product formed by emulsifying a hydrolyzed biomass is a desirable stable product comprising a nutrient. For example, with a *Schizochytrium* microorganism, which produces a dark orange, coffee-brown unstable emulsion upon hydrolysis (the dark color indicating less light scattering and larger droplets in the emulsion), it is actually desirable to further emulsify this hydrolyzed biomass to form a stable product comprising a nutrient. As a biomass hydrolysate is emulsified to a greater degree to form smaller droplets in the emulsion, the color of the product becomes lighter due to more light scattering. As such, the present invention further includes emulsifying the hydrolyzed biomass. The step of emulsification is conducted to form a stable product, i.e., a product that is more stable than a product formed from the biomass hydrolysate alone. For example, the stable product(s) of the present invention do not form separate phases upon standing, preferably for extended periods of time, and do maintain a uniform appearance and consistency as compared to the biomass hydrolysate alone. The emulsification step of the present invention increases the stability of the hydrolyzed material in that it creates a stable emulsion. Parameters by which to evaluate whether emulsions are stable are known in the art, and include assessing physical appearance, determining light scattering properties of the emulsion, assessing particle size of the dispersed phase, and/or performing centrifugation experiments. The stable emulsion of the present invention can stand at least about one day, more preferably at least about one week, more preferably at least about two weeks, more preferably at least about three weeks, and more preferably at least about four weeks at room temperature without forming separate phases. For example, the inventors have found that when the emulsification is carried out with a hydrolyzed *Schizochytrium* biomass, the formerly orange, coffee-brown hydrolysate forms an emulsion with enhanced stability that is a much lighter creamy tan in color. The stability of an emulsion is dependent on a complex series of factors including type of emulsifying agent, bulk viscosity of the solution, particle size of the dispersed phase droplets, temperature of the solution, concentration of the solution and so on. Although not wishing to be bound by theory, the present inventors believe that biomass includes components that act as particularly favorable emulsification agents that help stabilize the products of the present invention, as discussed in more detail below. The inventors further believe that the emulsification process of the biomass increases bulk viscosity, acts as a physical barrier and reduces the particle size of the dispersed phase, all of which can increase the stability of emulsifications. Furthermore, when emulsifying *Schizochytrium* biomass hydrolysate, the oil within the resulting emulsion can be a semi-solid at room temperature, further adding to the physical stability of the emulsion or the subsequent dried form of the composition.

Prior to emulsification, the hydrolyzed biomass may be further processed to allow for storage and/or for other reasons. For example, the hydrolyzed biomass may be optionally dewatered or concentrated to facilitate the emulsification step. The hydrolyzed biomass may be stored for a period of time for the convenience of the operators. Preferably, such hydrolyzed biomass is cooled and/or placed under an inert atmosphere for storage. Methods for replacement of air with inert atmospheres and appropriate freezing methods and temperatures are known in the art. For the emulsification step, in preferred embodiments, the hydrolyzed biomass may have up to about 99% or more moisture by weight. Preferably, the solids content is between about 5% to about 70%, more preferably about 10% to about 50%, most preferably about 15% to about 40%. The dried and/or concentrated and/or cooled hydrolyzed biomass may be reconstituted with water or any other preferred aqueous medium to a moisture content of any desired level before emulsification.

In one embodiment of further processing the hydrolyzed biomass, the biomass is treated to introduce browning reaction products (e.g., Maillard reaction products or caramelization products). Such browning reaction products can be produced and mixed into the hydrolyzed biomass. Alternatively, the biomass can be treated, e.g., by heating to produce or form the browning reaction products in the biomass, in which case precursors to the browning reaction products must be in the biomass, either by occurring naturally or by addition. For example, in the case of Maillard reaction products, amino acids and reducing sugars react at elevated temperature to form Maillard reaction products in well known reactions.

Emulsification of the hydrolyzed biomass-containing broth can be accomplished using methods for emulsification known in the art. Preferably, the emulsification process occurs without the addition of stabilizing agents and/or emulsifying agents such as fatty acids, phospholipids, amphiphilic molecules, surfactants, and/or thickening agents. The inventors have surprisingly found that the biomass hydrolysate products that are formed as a result of the hydrolysis process (e.g., cell particulates, seed materials, or animal tissue material) serve as excellent microencapsulants, emulsion stabilizers and oxidative stabilizers. Therefore, the use of added surfactants, emulsion stabilizers and microencapsulants is not required in order to produce the stable, emulsified and/or microencapsulated product of the present invention. Emulsification is the process of mixing immiscible liquids. Immiscible liquids will tend to maintain as small an interface as possible. Emulsions do not form spontaneously when liquids are mixed, but rather require energy input to break up the liquids, resulting in increased surface area of the internal phase. This energy input may be in the form of, for example, mechanical agitation such as, for example, mortar and pestle, colloid mill, rotor/stator, shear mixing, electric mixer, shaking, and preferably, homogenization; ultrasonic vibration; and/or heating. Preferably, the emulsion technique will be chosen to optimize for conditions resulting in stable emulsions. For example, if the emulsion is carried out with a high pressure homogenizer device, the type of valve should be chosen to enhance impingement and/or velocity and/or cavitation and/or turbulence and/or shear. A preferred method for emulsion comprises homogenization with a Panka2K homogenizer (Niro Inc., Hudson, Wis.), performing emulsification by passing hydrolysate through multiple passes at 1350 bar and 150 bar in the first and second stage, respectively. Both stages are preferably ball and ring-type emulsion heads. Alternatively, use of a microfluidizer at even higher pressures of up to 2500 bar may be preferable. In a further embodiment, the emulsion step can be conducted in a protective atmosphere (e.g. nitrogen) so as to limit contact of the product with oxygen which could cause degradation of the nutrient in the event that the nutrient is sensitive to oxidative degradation, such as LC PUFAs.

To maintain the emulsion after energy input, stabilizing and/or emulsifying agents (such as, for example, the cell particulates and other products of the hydrolyzed biomass) can be added. Emulsification agents are generally surface-active ingredients which tend to have molecules oriented between the two phases with the polar ends in the polar phase and the nonpolar ends in the nonpolar phase, which lowers the interfacial tension resulting in the miscibility of the two liquids. The methods by which emulsifying agents act to form emulsions are to reduce the interfacial tension, form a rigid interfacial film, and/or form an electrical double layer. If the emulsifier concentration is sufficiently high, a rigid film can be formed between the immiscible phases which can act as a mechanical barrier to coalescence of the droplets.

In preferred embodiments, the hydrolyzed biomass will act as a source of emulsification agents, i.e., the hydrolyzed biomass is an endogenous source of stabilizing agents such as emulsion stabilizers, surfactants, and/or microencapsulants. Although not required by the invention, stabilizing agents may be added to the hydrolyzed biomass prior to, during, or post-emulsification in order to provide enhanced stability, increased microencapsulation and an altered organoleptic profile of the resulting product. For example, such additional (exogenous) stabilizing agents include microencapsulants, surfactants, and emulsion stabilizers. Microencapsulants include, for example, proteins, simple and complex carbohydrates, solids and particulates. Preferred microencapsulants include cell particulates, gum acacia, maltodextrin, hydrophobically modified starch, polysaccharides, including alginate, carboxymethylcellulose and guar gum, hydrophobically-modified polysaccharides, such as octyl-substituted starches, proteins, including whey protein isolates, soy proteins, and sodium caseinate, and combinations thereof. Surfactants include, for example, anionic agents, cationic agents, nonionic agents, amphoteric agents, water-insoluble emulsifying agents, finely divided particles and naturally occurring materials. Anionic agents include carboxylic acids, sulfuric esters, alkane sulfonic acids, alkyl aromatic sulfonic acids, miscellaneous anionic hydrophilic groups; cationic agents include amine salts, ammonium compounds, other nitrogenous bases, non-nitrogenous bases; nonionic agents include an ether linkage to solubilizing group, ester linkage, amide linkage, miscellaneous linkage, multiple linkages; amphoteric agents include amino and carboxy, amino and sulfuric esters, amino and alkane sulfonic acids, amino and aromatic sulfonic acids, miscellaneous combinations of basic and acidic groups; water insoluble emulsifying agents include ionic hydrophilic groups, nonionic hydrophilic groups; finely divided particles include any finely divided non-solubilized particle including clays and carbon; naturally occurring materials include alginates, cellulose derivatives, water-soluble gums, lipids and sterols, phospholipids, fatty acids, alcohols, proteins, amino acids, detergents; and hydrophilic colloids. Emulsion stabilizers include emulsifiers and thickening agents. Thickening agents include polysaccharides. Thickeners are ingredients which are used to increase the viscosity of the continuous phase of the emulsions, and enhance emulsion stability by retarding movement of the droplets in the emulsion.

Additional ingredients may be added at any step in the method, including to the biomass, to the hydrolysate, or to the emulsified product. Preferably, they are added to the hydrolysate so that they can be blended with the biomass during the emulsification stage. Such ingredients include flavors or flavor enhancers, sweeteners, pigments, vitamins, minerals, pre-biotic compounds, pro-biotic compounds, therapeutic ingredients, functional food ingredients, food ingredients, proteins and/or processing ingredients.

In preferred embodiments, the emulsified products comprise an antioxidant. Antioxidants suitable for food, oils or fats preservation can be compatible with the present invention, and include vitamin E, butylhydroxytoluene (BHT), butylhydroxyanisole (BHA), tert-butylhydroquinone (TBHQ), vitamin C and derivatives thereof, phospholipids, and natural antioxidants such as rosemary extract, and combinations thereof. Preferred antioxidants include BHA, ascorbic acid, BHT, TBHQ, a blend of BHA/BHT, and combinations thereof. A preferred antioxidant comprises BHA and ascorbic acid. Amounts of antioxidant(s) to include in the composition will vary as suitable as determined by one skilled in the art.

In another preferred embodiment, emulsified products of the present invention may comprise a pharmaceutically active agent (i.e., a therapeutically, bioactive or medicinally active ingredient or combinations thereof). An added pharmaceutical agent, such as chondroitin or β-glucan, may also be used as a microencapsulant. Preferably, such emulsions are dried, such as by spray drying, to form microencapsulated products. This embodiment is particularly advantageous for pharmaceutically active agents which have low solubility in water. Such pharmaceutical products have the advantage of providing therapeutically active ingredients together with beneficial nutrients such as LC PUFAs. Pharmaceutically active agents of the present invention include, without limitation, statins, anti-hypertensive agents, anti-diabetic agents, anti-dementia agents, anti-depressants, anti-obesity agents, appetite suppressants and agents to enhance memory and/or cognitive function.

In another preferred embodiment, emulsified products of the present invention may comprise food ingredients such as functional food ingredients, food additives or other ingredients.

An important aspect of the present invention is that surprisingly, the inventors have found that the methods of the present invention provide a stable palatable emulsion of hydrolyzed biomass containing bioavailable nutrients, in particular omega-3 and/or omega-6 LC PUFAs. This stable palatable nutrient-containing emulsion can be achieved without the use of further processing steps to extract the desired nutrients, i.e., the stable palatable emulsion does not have to be further fractionated, processed, or separated for the purpose of enriching the hydrolyzed and/or emulsified biomass for any particular nutrient or component. This non-enriched emulsified composition can then be directly incorporated into a, or used as a, nutritional, cosmetic and/or pharmaceutical product of the present invention. Avoidance of further processing steps can confer a number of advantages. For example, the simplified methods of the present invention can eliminate extracting materials, reduce processing time, reduce safety/environmental issues from solvents and processing steps, achieve higher nutrient quality by reduction of processing times and processing materials, enhance stability of nutrients, reduce product losses, and lower costs. According to a preferred embodiment, the present invention provides for a method of producing a nutritional, cosmetic and/or pharmaceutical product rich in bioavailable nutrients, such as LC PUFAs, at costs greatly reduced compared with current methods of producing such products, which require further processing.

Although some embodiments of this invention include use of the product(s) made by the methods of the present invention without use of further processing steps to extract the desired nutrients, as explained above, the product(s) of the present invention may also be subjected to additional processing steps, e.g., to extract, fractionate and/or further purify a desired nutrient, such as an LC PUFA. Such methods for extraction/fractionation/purification are known in the art. For example, a hydrolyzed, emulsified, biomass can be dried to form a microencapsulated powder. A process to extract LC PUFAs from the dried powder, e.g., solvent extraction, would produce extracted LC-PUFA oil product, and also a defatted hydrolysate product. The defatted hydrolysate product can be desolventized and dried as needed. It could then be used as is in food or feed applications or could be further processed (purified, extracted, modified, etc.) for the generation of value added products. As a further example, a hydrolyzed, emulsified, biomass can be treated to recover minimally processed biomass. In this manner, the biomass hydrolysate emulsion of the present invention can function as a storage vehicle for nutrients, maintaining the nutrients in a stable state until needed when they can be removed from the biomass hydrolysate emulsion as described above. For example, the biomass hydrolysate emulsion can be stored under conditions to enhance stability of the product, such as at cold temperatures (e.g., less than room temperature or frozen), under non-oxidizing conditions (e.g., a reduced oxygen atmosphere, a nitrogen atmosphere or a carbon dioxide atmosphere) and/or in the absence of light (reduced light or darkness).

In a preferred embodiment, the emulsion of the present invention may optionally be dried directly and incorporated into a nutritional product, cosmetic product or pharmaceutical product. Spray drying is the preferred method of drying to produce the dry composition of the present invention. Accordingly, the present invention includes a dry composition comprising a biomass hydrolysate. This dry composition can exist in a variety of forms such as, for example, a powder, pellets, granules, tablets, agglomerates, noodles, shaped forms, bars, sheets and have a water content of about 0% to about 30%. The inventors believe, without being bound by theory, that the methods of the present invention result in a stable dry composition due to the presence of materials derived from the biomass, and that the materials from the biomass serve as excellent microencapsulants protecting the nutrient(s) from degradation, including oxidative degradation, by forming a matrix that dries around the nutrient (especially when the nutrient is a PUFA, preferably a LC PUFA). Traditionally, food products can be enriched with PUFAs by supplementing the products with PUFA oils. However, when dry forms of the PUFAs are required, the oils must be further processed to form, for example, a microencapsulated powder that is suitable for use in various food applications. The present invention provides a dry, LC PUFA rich composition, and a process for making said composition that does not require extracting PUFAs from their native source prior to use or subsequently processing the extracted PUFA oil to produce a dry composition. Thus, the dry PUFA product of the present invention can be made using safe materials, minimal processing steps, reduced processing time, fewer processing materials and using a process that involves fewer product losses and lower costs. The present invention also provides for a nutritional product (including a vitamin or a multivitamin), a cosmetic product and/or a pharmaceutical product produced by methods of the present invention.

The stable emulsion or the dried composition of the present invention may be used alone as a nutritional product, cosmetic product or pharmaceutical product or may be incorporated or added to a nutritional, cosmetic or pharmaceutical product. In a first embodiment, the product produced is a nutritional product, such as a food product or a nutriceutical. The product may be used directly as a food ingredient, such as an ingredient in beverages, sauces, dairy based foods (such as milk, yogurt, cheese and ice-cream) and baked goods; or alternately used as a nutritional product, e.g., as a nutritional supplement (chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules); feed or feed supplement for any companion animal or pet; feed or feed supplement for any animal whose meat or products are consumed by humans; food supplement, including baby food and infant formula. The term "animal" means any organism belonging to the kingdom Animalia and includes, without limitation, any animal from which poultry meat, seafood, beef, pork or lamb is derived. Seafood is derived from, without limitation, fish, shrimp and shellfish. The term "products" includes any product other than meat derived from such animals, including, without limitation, eggs, milk or other products. When fed to such animals, nutrients such as LC PUFAs can be incorporated into the flesh, milk, eggs or other products of such animals to increase their content of these nutrients.

For example, the liquid emulsion or the dry composition of the present invention can be incorporated into a liquid food product. The liquid food product with incorporated emulsion or dry composition can be used as-is or dried using any method, including those discussed herein, such as spray drying or injection of the liquid hydrolysate with optional added dry agents in an extrusion process. The liquid emulsion or the dry composition of the present invention can be added to a wide range of products such as baked goods, vitamin supplements, diet supplements, powdered drinks, etc. at various stages of production. The dry composition of the present invention can be in the form of a powder and can be modified using methods such as crosslinking, tableting, denaturing, agglomeration, etc. to produce a modified powder. The powder can also be modified to obtain, for example, a water-, heat-, shearing-, pH-, and/or pressure-resistance to produce a functional powder. These modifications can be performed/obtained using methods such as, for example, radiation treatment, heat treatment, chemical treatment, physical treatment, cross-linking, and coating. The powder form or modified powder form of the product can be added to dry form products, slurried with non-solid products, and/or slurried with non-solid products and dried. The liquid emulsion can be further modified using methods including, but not limited to, heat treatment, crosslinking, filtration and coacervation to produce a modified liquid emulsion. The liquid emulsion or modified liquid emulsion can be added to dry form products, added to dry form products then dried, added to liquid form products, or added to liquid form products then dried.

Numerous finished or semi-finished powdered food products can be produced by drying liquid compositions via spray drying or other drying methods, and the liquid emulsion of the present invention can be added to the liquid form of these products prior to their drying. This allows the incorporation of the hydrolyzed biomass into the final dry product, such as, for example, infant formula powders, baby food mixes, infant food mixes, skim milk powder, dry beverages, or any other food where drying is involved. Another embodiment includes skim milk powder containing biomass emulsion comprising nutrients as a low cost alternative in providing products with such nutrients to developing or poor countries. Likewise, the liquid hydrolyzed biomass could also be incorporated in finished or semi-finished liquid food products at different steps of the production process.

A partial list of food products comprising the products of the present invention includes doughs, batters, baked food items including, for example, such items as cakes, cheesecakes, pies, cupcakes, cookies, bars, breads, rolls, biscuits, muffins, pastries, scones, and croutons; liquid food products, for example, beverages, energy drinks, infant formula, liquid meals, fruit juices, multivitamin syrups, meal replacers, medicinal foods, and syrups; semi-solid food products such as baby food, yogurt, cheese, cereal, pancake mixes; food bars including energy bars; processed meats; ice creams; frozen desserts; frozen yogurts; waffle mixes; salad dressings; and replacement egg mixes. Also included are baked goods such as cookies, crackers, sweet goods, snack cakes, pies, granola/snack bars, and toaster pastries; salted snacks such as potato chips, corn chips, tortilla chips, extruded snacks, popcorn, pretzels, potato crisps, and nuts; specialty snacks such as dips, dried fruit snacks, meat snacks, pork rinds, health food bars and rice/corn cakes; and confectionary snacks such as candy.

Another product embodiment of the present invention is a cosmetic product. A cosmetic product includes a product which is in a formulation to be administered in a topical application. Exemplary products include sun screens, face creams, hand creams, moisturizers, foundations, eye gels and shaving creams.

Another product embodiment of the present invention is a pharmaceutical product. A pharmaceutical product includes a product which is in a formulation to be administered under the supervision of a physician and which is intended for the specific management of a disease or condition for which distinctive nutritional requirements, based on recognized scientific principles, are established by medical evaluation.

The dry form of the product can be functionalized using various methods. For example, one method would be to heat the liquid or dry form of the product to quicken reactions between reducing sugars and proteins to form a myriad of Maillard products. Heating may also incite crosslinking with the presence of crosslinking agents, such as enzymes, that may be added, but also may occur naturally in the system, such as bisaldehydes. Preferably, the resultant product can have increased shear-resistance, oxidation-resistance, pressure resistance and/or an improved flavor and color. As another example, coating the particulates can be done to functionalize the product. Techniques such as fluid bed coating, co-extrusion, coacervation could be used. Preferably, fluid bed "Wurster"-style coating can be performed with a starting solid form to apply a coating that would provide/enhance the desired product characteristics. For example, if the product is water soluble, a water insoluble coating can be applied, thus producing a water-resistant product form. Chemical treatments can include, for example, pH shifting of the product. Acidifying the products can enhance their oxidative stability.

The dried or semi-dried emulsion may also be agglomerated. The term 'agglomeration' refers to the process of forming larger particles from smaller ones, and may be accomplished by pelletizing, extruding, granulating, or otherwise forming larger particles of the emulsified biomass. To prepare for an agglomeration step, the emulsion may optionally have its moisture content adjusted, so that the moisture level is between about 5% and about 50% by weight, preferably between about 5% and about 20%, and most preferably between about 5% and about 15%. If the moisture content is higher than desired, the emulsion can optionally be mechanically or thermally (i.e. evaporation) dewatered. Preferably, to obtain a suitable moisture level, a dry agent is added to the emulsion. The addition of a dry agent confers a number of advantages besides simply lowering moisture level, including, for example, improving the consistency of the emulsion, or acting as a binder to help retain the integrity of an agglomerated product. The dry agent may be added to the emulsion at a final concentration of between about 1 weight percent and about 50 weight percent (dry weight). Preferred amounts to add are between about 5 weight percent and about 30 weight percent. In one embodiment, the porosity is such that about 50% of the volume of the particle comprises air.

Suitable dry agents include any agent that decreases the overall moisture of the emulsion. Preferred agents include plant starches, such as wheat bran, oats and rice flour; plant fibers such as cellulose; biomeals derived from, for example, microorganisms or plant proteins; and oilseed hulls such as peanut, soybean or cottonseed hulls. Preferred dry agents include rice flour and peanut hulls. The dry agent may be added at some point after emulsifying. Mixing of the dry agent with the emulsion may be accomplished by methods known in the art. The emulsion, with added dry agent can be agglomerated. A number of agglomeration techniques may be employed. Any appropriate agglomeration technique that leads to particles with the desired qualities is compatible with the present invention.

The emulsions, liquid or dried, of the present invention may additionally be extruded. Extrusion may be accomplished by any method known in the art. In one method, the food material is fed into the extruder through a feed hopper. A tapered, rotating screw moves the food material and compresses it, causing it to heat up at the same time. The gradual decrease in the flight depth or the pitch achieves compression in the transition section. Following the compression section is the metering section which is the part nearest to the discharge of the extruder, where often expansion ('puffing') of the food material occurs. Extruders typically have different injection (or feeding) ports along the barrel. The right injection (or feeding) port is selected based on degree of mixing or sheer needed, temperature exposure needed, and product sensitivity or application. The liquid emulsion can be injected at any injection port based on the above factors. Alternatively, the liquid emulsion or the dried composition of the present invention can be added to the pre-mix prior to extrusion. Alternatively, the emulsion of the dried form of the present invention can be added to a product post extrusion. Suitable extruded food products include, for example, food bars including energy bars, pastas, ready-to-eat cereals, confectionery products, baby foods and instant foods, beverage bases and texturized vegetable proteins.

In preferred embodiments, the products of the present invention are stored under appropriate conditions to minimize oxidative degradation. Many methods to effect such storage conditions are suitable for use with the present invention, such as, for example, replacement of ambient air with an inert gas atmosphere. A preferred method by which to reduce or minimize oxidative degradation is to store products under a nitrogen ($N_2$) atmosphere or mixed nitrogen and carbon dioxide atmosphere or under vacuum. Preferably, packaged products are packaged under nitrogen. Methods for producing a nitrogen gas atmosphere into a container comprising a product are known in the art.

The present invention, while disclosed in terms of specific methods, products, and organisms, is intended to include all such methods, products, and organisms obtainable and useful according to the teachings disclosed herein, including all such substitutions, modifications, and optimizations as would be available to those of ordinary skill in the art. The following examples and test results are provided for the purposes of illustration and are not intended to limit the scope of the invention.

EXAMPLES

Example 1

This Example shows the production of a dry powder composition made by drying a biomass hydrolysate emulsion without use of added emulsifiers, stabilizers or microencapsulants.

733.5 grams (g) water was added to 400 g dried *Schizochytrium* biomass to reconstitute fermentation broth. While stirring via an air driven, double impeller overhead mixer, the system was allowed to reach 63° C. (approx. 30-45 min). 7.45 g of 0.5 wt % ALCALASE™/TOTAL system (available from Novozyme, Bagsvaerd, Denmark) was then added. Immediately, the viscosity of the system decreased and pH dropped from ~7 to ~6.4. Using 50% caustic, the system was adjusted to maintain a pH of 7.2 throughout the duration of hydrolysis. The system mixed for 90 minutes at that temperature and pH.

A Panka2K homogenizer (Niro, Hudson, Wis.) emulsified the liquid in 4 passes at 1350 bar and 150 bar in the first and second stage, respectively. Using multiple passes at such a high pressure produced an emulsion that was very hot (~90-100° C.). Both stages were ball and ring-type emulsion heads. The slurry became more white and thick from processing, from the brownish-orange color it was. The emulsion had 31.76% solids and weighed 991.5 grams (g), all of which was spray dried.

A Buchi B-290 spray dryer (lab spray dryer) dried the emulsion down from 31.76% solids to ~2.5% moisture, using 150° C. inlet air temperature, maximum air flow, 40 units atomizing air, collection-style main chamber, 94° C. outlet air temperature, collection-style cyclone, and operating in suction mode. Of the theoretical 314.9 g of solids, 108.3 g were collected below the cyclone and 177.2 g collected by brushing down the chamber. The rest of the material was stuck to the interior walls of the spray dryer. Only the powder in the cyclone and cyclone collection pot was used for powder analysis. The powder had a bulk density of 309.1 kg/m$^3$ and a tap density (300 tap) of 364.3 kg/m$^3$.

Example 2

This Example shows the production of a dry powder composition made by drying a biomass hydrolysate emulsion comprising added emulsifiers, stabilizers and microencapsulants.

Approximately 833 mL of fermentation broth comprising *Schizochytrium* was stirred using an air driven, single impeller overhead mixer, and allowed to reach 63° C. (approx. 30-45 min.). 4.22 g of 0.5 wt % ALCALASE™/TOTAL system was then added to the broth. Immediately, the viscosity of the system decreased and pH dropped from ~7 to ~6.4. Using 50% caustic, the system was adjusted to maintain a pH of 7.2. The system mixed for 45 minutes at that temperature and pH.

The broth temperature was then lowered to 45° C. A high-shear mixer incorporated the following ingredients in the order as listed: (1) 0.5090 g Artificial Bitterness Masker (ABM) and 2.5121 g Orange Oil Extract (OOE), (2) 20 g High Fructose Corn Syrup-55 (HFCS-55), (3) 20 g Maltodextrin DE-4 and 22.5 g Gum Arabic, (4) 12.5 g Ascorbic Acid, (5) 50 g whey protein isolates (WPI). The protein was allowed to hydrolyze and hydrate after addition over a period of 45 minutes at 45° C.

A Panka2K homogenizer (Niro) emulsified the liquid in a single pass at 1350 bar and 150 bar in the first and second stage, respectively. Both stages were ball and ring-type emulsion heads. The slurry, which was brownish-orange in color, became more white and thick due to processing. The emulsion had 28.00% solids and weighed 490.1 g, all of which was spray dried.

The Buchi B-290 spray dryer (lab spray dryer) dried the emulsion down from 28.00% solids to 2.69% moisture, using 150° C. inlet air temperature, maximum air flow, 40 units atomizing air, collection-style main chamber, 93° C. outlet air temperature, collection-style cyclone, and operating in suction mode. Of the theoretical 137.23 g of solids, 63.2 g were collected below the cyclone and 54.5 g collected by brushing down the chamber. The rest of the material was stuck to the interior walls of the spray dryer. Only the powder in the cyclone and cyclone collection pot was used for powder analysis. The powder had a bulk density of 300 kg/m$^3$ and a tap density (300 tap) of 480 kg/m³. It contained 98.5 mgDHA/g of powder, 25.01% protein, 4.67% ash, 27.5% fat, and 39.09% carbohydrate. The powder had 0.81% free oil, yielding an encapsulation efficiency of 97.1%. Its sensory profile was favorable with an orange aroma, and no fishy/painty notes.

Example 3

This Example shows the production of a dry powder composition made by drying a biomass hydrolysate emulsion comprising added emulsifiers, stabilizers and microencapsulants.

500.0 g of water was added to 125 g dried *Schizochytrium* biomass to reconstitute fermentation broth. The system was allowed to reach 63° C. while stirring with an air driven, single impeller overhead mixer (approx. 30-45 min.). 3.2 g of 0.5 wt % ALCALASE™/TOTAL system was then added. Immediately, the viscosity of the system decreased and pH dropped from ~7 to ~6.4. Using 50% caustic, the system was adjusted to maintain a pH of 7.2. The system was mixed for 90 minutes at that temperature and pH.

The broth temperature was then lowered to 45° C. A high-shear mixer incorporated the following ingredients in the listed order: (1) 45 g whey protein isolate (WPI), (2) 18.8 g High Fructose Corn Syrup-55 (HFCS-55), (3) 6.25 g Maltodextrin DE-4 and 25.0 g Gum Arabic, (4) 2.5 g Ascorbic Acid, (5) 1.0 g Artificial Bitterness Masker (ABM) and 1.5 g Orange Oil Extract (OOE). The protein was allowed to hydrolyze and hydrate after addition over a period of 30 minutes at 45° C.

A Panka2K homogenizer (Niro) emulsified the liquid in a single pass at 1350 bar and 150 bar in the first and second stage, respectively. Both stages were ball and ring-type emulsion heads. The slurry became more white and thick from processing, from the brownish-orange color it was. The emulsion had 36.57% solids and weighed 587.8 g, 540.5 g of which was spray dried.

The Buchi B-290 spray dryer (lab spray dryer) dried the emulsion down from 36.57% solids to 2.73% moisture, using 150° C. inlet air temperature, maximum air flow, 40 units atomizing air, collection-style main chamber, 94° C. outlet air temperature, collection-style cyclone, and operating in suction mode. Of the theoretical 197.7 g of solids, 67.4 g were collected below the cyclone and 111.2 g collected by brushing down the chamber. The rest of the material was stuck to the interior walls of the spray dryer. Only the powder in the cyclone and cyclone collection pot was used for powder analysis. The powder had a bulk density of 300 kg/m³ and a tap density (300 tap) of 413 kg/m³. It contained 1113.6 mgDHA/g of powder, and 31.1% fat. The powder had 0.85% free oil, yielding an encapsulation efficiency of 97.3%. Its sensory profile was favorable with an orange, milky and nutty aroma, and no fishy/painty notes.

Example 4

This Example shows the production of a dry powder composition using *Schizochytrium* microorganisms lysed in broth by mechanical means, supplemented with added ingredients, emulsified, and then spray dried.

To 355 g of dried *Schizochytrium* biomass was added 1029 g of water. The solution was mixed and homogenized through a Niro Panda 2k homogenizer with a "knife" edge processing valve at 1000 bar. The resultant hydrolysate was supplemented with 50 g of high fructose corn syrup, 102 g of whey protein isolate, 12 g of maltodextrin, 52 g of gum arabic, and 5.5 g of ascorbic acid under stirring via a high sheer mixer. The solution was allowed to mix for 45 minutes at room temperature.

A Panka2K homogenizer (Niro) emulsified the liquid in a two passes at 1350 bar and 150 bar in the first and second stage, respectively. Both stages were ball and ring-type emulsion heads. The slurry became more white and thick from processing, from the brownish-orange color it was. During the emulsion preparation, 721.31 g of water was added. The emulsion had 24.49% solids and weighed 1582.9 g, all of which was spray dried.

The Buchi B-290 spray dryer (lab spray dryer) dried the emulsion down from 24.49% solids to 0.99% moisture, using 160° C. inlet air temperature, maximum air flow, 40 units atomizing air, collection-style main chamber, 77° C. outlet air temperature, collection-style cyclone, and operating in suction mode. Of the theoretical 387.7 g of solids, 192.57 g were collected below the cyclone and 137.86 g collected by brushing down the chamber. The rest of the material was stuck to the interior walls of the spray dryer. Only the powder in the cyclone and cyclone collection pot was used for powder analysis. The powder had a bulk density of 267 kg/m³ and a tap density (300 tap) of 406 kg/m³. It contained 102.6 mgDHA/g of powder, and 26.0% fat. The powder had 0.31% free oil, yielding an encapsulation efficiency of 98.8%. Its sensory profile was favorable with a milky and nutty aroma, and no fishy/painty notes.

Example 5

This Example shows the production of a dry powder composition using *Schizochytrium* lysed in broth by FLAVOURZYME® (Novozymes, Bagsvaerd, Denmark), supplemented with added ingredients, emulsified, and then spray dried.

994 g of water was added to 355 g dried *Schizochytrium* biomass to reconstitute fermentation broth. To 355 g of dried *Schizochytrium* biomass was added 994 g of water. The solution was heated to 60° C. and FLAVOURZYME (Novozymes) was added at a 0.5% w/w rate (6.7 g). Maintaining a pH of 7.2, the mixture was stirred for 50 minutes.

The broth temperature was then lowered to 45° C. A high-shear mixer incorporated the following ingredients in the listed order: (1) 102 g whey protein isolate (WPI), (2) 50 g High Fructose Corn Syrup-55 (HFCS-55), (3) 12 g Maltodextrin DE-4 and 52 g Gum Arabic, (4) 5.5 g Ascorbic Acid.

A Panka2K homogenizer (Niro) emulsified the liquid in three passes at 1350 bar and 150 bar in the first and second stage, respectively. Both stages were ball and ring-type emulsion heads. The slurry became more white and thick from processing, from the brownish-orange color it was. The emulsion had 31.10% solids and weighed 1490.67 g, all of which was spray dried.

The Buchi B-290 spray dryer (lab spray dryer) dried the emulsion down from 31.10% solids to 1.79% moisture, using 160° C. inlet air temperature, maximum air flow, 40 units atomizing air, collection-style main chamber, 90° C. outlet air temperature, collection-style cyclone, and operating in suction mode. Of the theoretical 463.6 g of solids, 229.4 g were collected below the cyclone and 192.8 g collected by brushing down the chamber. The rest of the material was stuck to the interior walls of the spray dryer. Only the powder in the cyclone and cyclone collection pot was used for powder analysis. It contained 115.6 mgDHA/g of powder, and 28.9% fat. The powder had 1.1% free oil, yielding an encapsulation efficiency of 96.3%. Its sensory profile was favorable with an orange, milky and nutty aroma, savory flavor and no fishy/painty notes.

Example 6

This Example shows the production of a dry powder composition using *Schizochytrium* microorganisms and an instant soy meal replacement as an encapsulant to make a soy supplement powder with the biomass hydrolysate emulsion.

To 100.1 g of dried *Schizochytrium* biomass was added 705.2 g of water. The resultant solution was stirred gently, shear mixed, then homogenized. The shear mixing was done with an L4RT-A batch lab shear mixer (Silverson Machines) at 6.5 kRPM for 5 minutes. The homogenization (i.e. cell lysis) was carried out with a Panda 2k homogenizer (Niro-Soavi) at 1000 bar with a "knife-edge" valve in the first stage and a blank valve the second stage. 16.21 g of the resultant broth mixture was added to 695.3 g of water. Under shear mixing (3.5 kRPM for 5 minutes in said shear mixer), 117 g (3 servings) of Natureade® Total Soy Meal Replacement, Strawberry Créme flavor was added. After incorporation, the solution was allowed to hydrate for 30 minutes under same mixing conditions. The resultant solution was homogenized in the Panda 2k with 3 passes at 1500 bar with the heat generated from homogenization exchanged with excess cooling fluid at 60° C.

The emulsion was then spray dried with a Buchi B-290 spray dryer with a 170° C. inlet air temperature and an 83° C. outlet temperature. The feed pump ran at 30 RPM and the feed was atomized with 30 units atomizing air.

A portion of the powder was collected for testing. The sensory profile was acceptable compared to the original powder and there was no detectable free oil. The final DHA loading was 150 mgDHA/serving.

Example 7

This example shows the use of the biomass hydrolysate emulsion in an extruded fruit loop cereal.

To 210 lbs of corn flour was added 180 lbs of wheat flour, 150 lbs of oat flour, 48 lbs of sugar, 12 lbs of salt and 150 lbs of water. A hydrolysate emulsion that contained 11% DHA by weight was mixed with a portion of this batter in such a manner as to generate fruit loops with 35 mgDHA/30 g serving.

The dough was batched to a TX-57 twin screw extruder from Wenger Manufacturing, Inc. The screw turned at 301 rpm with the three heating zones set to 50, 80 and 120° C. The dough was cut with a knife at the die on the extruder. The loops were dried in an oven with ambient air blowing over them for 6 minutes. At this point, the loops were coated with sugar syrup with fruit flavor according to the following recipe: 44 lbs of sugar, 18.7 lbs of water, and 1.65 lbs of fruit flavor. The cereal was coated in a tumbler under mixing with a high volume low pressure compressed air paint gun applying the sugar solution.

After a final drying at 105° C. for 5 minutes, the cereal was vacuum sealed in plastic packaging. The sensory profile and stability were acceptable.

Example 8

This Example describes the production of a non-fat dried milk product comprising the biomass hydrolysate emulsion of the present invention.

A hydrolysate emulsion of the present invention made from *Schizochytrium* biomass (1.657 g with 28.4% solids) containing 14.5% DHA (solids basis) was added to 473 g of Kroger Seal Test™ Skim Milk to produce a skim milk with 35 mgDHA/serving. This mixture was spray dried on a Buchi B-290 spray dryer with an inlet temperature of 170° C. and outlet temperature of 70° C. with the fan running at 100%. The hydrolysate emulsion skim milk powder was collected and used in two food systems, as described below.

The hydrolysate emulsion skim milk powder (25.4 g) was added to water (214.6 g) to prepare reconstituted skim milk. One half of this hydrolysate emulsion skim milk was supplemented with Ovaltine® (10.5 g) to produce a skim milk chocolate malt drink.

The reconstituted skim milk, the skim milk chocolate malt drink and the hydrolysate skim milk powder were taste tested. All three had acceptable taste.

Example 9

This Example shows the preparation of a hydrolysate emulsion powder using enzymatic hydrolysis and browning reactions to modify the flavor of the resultant powder. Fermentation broth comprising *Schizochytrium* microorganisms was washed with three times its weight in water and centrifuged at 4600RCF for 7 minutes. The supernatant was poured off and concentrated broth collected. 540.5 g of this broth was added to 387.0 g of water. This mixture was stirred with an air driven mixer with 2 impellers on a hot plate at 55° C. Once the liquid reached this temperature, Alcalase® from Novozymes was added at 0.5% enzyme liquid to total liquid weight. The pH was adjusted to 7.0 and was allowed to react for one hour. At that point, to enhance the cell/protein lysis, the liquid was heated to 85° C. and held there for 15 minutes. This step denatures the proteins. After the 15 minutes, the mixture was allowed to cool down to 60° C. under constant stirring. At that point, another treatment of Alcalase® was conducted in the presence of Flavourzyme® (also from Novozymes) which was added at 2% enzyme liquid to total liquid weight. This mixture was allowed to react for 2 hours. This time was believed to be sufficient to allow the enzymatic reactions to proceed to completion. The Alcalase® acted on the previously denatured proteins to further the degree of hydrolysis. After the two hours, the broth was heated to 95° C. and pH brought up to 9.5 with caustic soda solution. Once up to temperature, 32.4 g of lactose, 34.1 g of maltodextrin, and 42.0 g of high fructose corn syrup-55 were added. This step inactivates the enzymes, promotes further protein hydrolysis, and the combination of protein hydrolysis products with the sugars results in browning reaction products (e.g., Maillard reaction products and caramelization products). Without being bound by theory, it is believed that intact proteins in the biomass can be the source of undesirable flavors, and that enzymatically and chemically changing the proteins alters their taste profile. This mixture was allowed to react for 2 hours then allowed to cool to 60° C. Upon cooling, 17.3 g of Martek DHA-S™ oil (Martek Biosciences Corporation, Columbia, Md.) containing 2.6 g of polysorbate 80, 2.6 g of orange oil, 2.6 g of artificial bitterness masker, and 0.8 g of TAP1010 (high oleic sunflower oil with 10% mixed tocopherols and 10% ascorbyl palmitate) was added. After allowing the oil and treated biomass to mix for 15 minutes, the mixture was supplemented with 35 g of casein.

This mixture was homogenized at 750 bar in a Panda 2k homogenizer (Niro-Soavi) with emulsion style valves in both stages (680/70) for 3 passes maintaining a temperature of 60° C. Upon completion, 3.2 g of artificial vanilla flavoring was added with gentle stirring with a spatula. The resultant broth was then spray dried in a Buchi B-290 spray dryer with an inlet temperature of 170° C. and an outlet temperature of 70° C. with the fan operating at 100% capacity. The powder was collected. The "as-is" powder tasted and smelled acceptable.

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the foregoing best mode of carrying out the invention should be considered exemplary in nature and not as limiting to the scope and spirit of the invention as set forth in the appended claims.

What is claimed is:

1. A method for producing a stable liquid emulsion comprising at least one long-chain polyunsaturated fatty acid (LC-PUFA), said method comprising:
   a) hydrolyzing a microbial biomass comprising the at least one LC-PUFA to produce a hydrolyzed biomass comprising the at least one LC-PUFA and microbial cell particulates wherein said microbial biomass is a microorganism of the genus *Schizochytrium*; and
   b) emulsifying the hydrolyzed biomass to form a stable liquid emulsion comprising the at least one LC-PUFA and the microbial cell particulates wherein the stable liquid emulsion does not form separate phases after storage at room temperature for at least one week.

2. The method of claim 1, comprising drying the stable liquid emulsion.

3. The method of claim 2, wherein the stable emulsion comprising the at least one LC-PUFA and the microbial cell particulates is dried by a method selected from the group consisting of membrane filter press drying, spray drying, fluidized bed drying, lyophilization, freeze drying, tray drying, vacuum tray drying, drum drying, vacuum mixer/reactor drying, excipient drying, solvent drying, fluidized spray drying, conveyer drying, ultrafiltration, evaporation, osmotic dehydration, freezing, absorbent addition, extrusion and a combination thereof.

4. The method of claim 1, wherein the stable emulsion is extruded.

5. The method of claim 3, wherein a stabilizing agent is added to said stable liquid emulsion prior to drying the stable emulsion.

6. The method of claim 5, wherein the stabilizing agent is selected from the group consisting of microencapsulants, surfactants, emulsion stabilizers and a combination thereof.

7. The method of claim 1, wherein the hydrolyzing the microbial biomass is selected from the group consisting of enzymatic hydrolysis, chemical disruption, physical-mechanical disruption, physical-non-mechanical disruption and a combination thereof.

8. The method of claim 1, wherein the hydrolyzing the microbial biomass is enzymatic hydrolysis.

9. The method of claim 1, wherein the hydrolyzing the microbial biomass is chemical disruption.

10. The method of claim 1, wherein the hydrolyzing the microbial biomass is physical-non-mechanical cell disruption.

11. The method of claim 1, further comprising contacting browning reaction products with the hydrolyzed biomass.

12. The method of claim 1, wherein the emulsifying is selected from the group consisting of mechanical agitation, ultrasonic vibration, heating, and combinations thereof.

13. The method of claim 1, wherein the at least one LC-PUFA has a carbon chain length of at least 18.

14. The method of claim 13, wherein the at least one LC-PUFA has a carbon chain length of at least 22.

15. The method of claim 13, wherein the at least one LC-PUFA comprises an LC-PUFA selected from the group consisting of docosahexaenoic acid, docosapentaenoic acid, arachidonic acid, eicosapentaenoic acid, gamma-linolenic acid, and mixtures thereof.

16. The method of claim 1, wherein the stable liquid emulsion produced is more stable than the hydrolyzed biomass before b).

17. The method of claim 1, further comprising adding an ingredient selected from the group consisting of flavors, flavor enhancers, sweeteners, pigments, vitamins, minerals, pre-biotic compounds, pro-biotic compounds, therapeutic ingredients, medicinal ingredients, functional food ingredients, food ingredients, and combinations thereof.

18. The method of claim 1, further comprising pretreating the microbial biomass.

19. The method of claim 18, wherein the pretreating the microbial biomass is selected from the group consisting of pasteurization, heat shocking, washing, adding antioxidants, pH adjusting, adding omega-3 fatty acids, shearing/cell weakening and combinations thereof.

20. The method of claim 1, wherein the microbial biomass is previously dried and reconstituted.

21. The method of claim 1, wherein the microbial biomass is in a fermentation broth.

22. A method for producing a stable liquid emulsion comprising a long-chain polyunsaturated fatty acid (LC-PUFA), said method comprising:
   a) hydrolyzing a microbial biomass comprising the LC-PUFA to produce a hydrolyzed biomass comprising the LC-PUFA and microbial cell particulates wherein said microbial biomass is a microorganism of the genus *Schizochytrium*;
   b) emulsifying the hydrolyzed biomass to form a stable liquid emulsion comprising the LC-PUFA and the microbial cell particulates wherein the stable liquid emulsion does not form separate phases after storage at room temperature for at least one week; and
   c) storing the stable liquid emulsion.

23. The method of claim 1, wherein the microbial cell particulates are selected from the group consisting of cell membrane fragments, nuclei fragments, intracellular components, and mixtures thereof.

24. The method of claim 22, wherein the microbial cell particulates are selected from the group consisting of cell membrane fragments, nuclei fragments, intracellular components, and mixtures thereof.

* * * * *